US007285248B2

(12) United States Patent
Yamamoto et al.

(10) Patent No.: US 7,285,248 B2
(45) Date of Patent: Oct. 23, 2007

(54) FAN TYPE CHEMICAL DISPERSION EQUIPMENT

(75) Inventors: Kazunori Yamamoto, Hiroshima (JP); Satoshi Yamasaki, Hiroshima (JP)

(73) Assignee: Fumakilla Limited, Tokyo (JP)

( * ) Notice: Subject to any disclaimer, the term of this patent is extended or adjusted under 35 U.S.C. 154(b) by 722 days.

(21) Appl. No.: 10/381,916

(22) PCT Filed: Sep. 21, 2001

(86) PCT No.: PCT/JP01/08261

§ 371 (c)(1),
(2), (4) Date: Mar. 28, 2003

(87) PCT Pub. No.: WO02/060246

PCT Pub. Date: Aug. 8, 2002

(65) Prior Publication Data

US 2003/0175171 A1 Sep. 18, 2003

(51) Int. Cl.
*A62B 7/08* (2006.01)
(52) U.S. Cl. .................. 422/123; 239/57; 261/30; 261/104; 422/124
(58) Field of Classification Search ............... 422/123, 422/124; 261/30, 104; 239/57
See application file for complete search history.

(56) References Cited

U.S. PATENT DOCUMENTS 4,035,451 A  7/1977  Tringali
4,857,240 A *  8/1989  Kearnes et al. ............... 261/26
5,422,078 A *  6/1995  Colon ........................ 422/123
6,719,217 B1 *  4/2004  Tawara et al. ............ 239/419.5

FOREIGN PATENT DOCUMENTS

| JP | 56-117688 | 2/1955 |
| JP | 53-14329 | 2/1978 |
| JP | 53-58193 | 5/1978 |
| JP | 62-175879 | 11/1987 |
| JP | 05-153892 | 6/1993 |
| JP | 06-55795 | 8/1994 |
| JP | 08-154554 | 6/1996 |

(Continued)

OTHER PUBLICATIONS

International Preliminary Examination Report dated Apr. 16, 2003; International Application No. PCT/JP/0108261 filed Sep. 21, 2001.

*Primary Examiner*—Krisanne Jastrzab
(74) *Attorney, Agent, or Firm*—Frishauf, Holtz, Goodman & Chick, P.C.

(57) ABSTRACT

A fan type chemical dispersion equipment, wherein a chemical container (3) and a power supply storage body (2*a*) are disposed detachably from an equipment body (1) and so as not to be volumetrically limited with each other, whereby, because the equipment body, chemical container, and power supply storage body can be volumetrically formed independently of each other, the settings of a chemical holding amount relative to a fan air blow amount and long or short service time can be performed easily, the chemical container being capable of preventing a chemical impregnated body from being caught between the end face of a chemical container body (3*a*) and a cover body (3*b*), and a clip device being capable of firmly fixing the fan type chemical dispersion equipment to the held materials ranging from thin to thick ones.

26 Claims, 24 Drawing Sheets

FOREIGN PATENT DOCUMENTS

| | | |
|---|---|---|
| JP | 3040513 | 6/1997 |
| JP | 10-190510 | 7/1998 |
| JP | 11-103749 | 4/1999 |
| JP | 11-308955 | 11/1999 |
| JP | 3068017 | 2/2000 |
| JP | 3071666 | 6/2000 |
| JP | 3071760 | 6/2000 |

\* cited by examiner

FAN TYPE CHEMICAL DISPERSION EQUIPMENT

This application is a U.S. National Phase of International Application No. PCT/JP01/08261 filed on Sep. 21, 2001.

BACKGROUND OF THE INVENTION

1. Technical Field

The present invention relates to a fan type chemical diffusing apparatus for volatilizing and diffusing a chemical in an airflow produced by a motor driven fan or blower, and a receptacle for the chemical for use with such a fan type chemical diffusing apparatus, as well as a clip type fastening device for fastening a fan type chemical diffusing apparatus to an object such as apparel of its user.

2. Description of the Prior Art and Objects of the Invention

A fan type chemical diffusing apparatus designed to volatilize and diffuse a chemical in an airflow produced by a motor driven fan has been known as described in JP S53-14329 A.

The apparatus described in that patent literature comprises a cylindrical housing that constitutes an apparatus main body equipped with a motor and fan, in which a cartridge is interchangeably loaded. That contains a battery and a chemical retainer which holds a chemical therein. The fan is driven by the motor to produce an airflow with which the chemical in the cartridge is allowed to volatilize and diffuse into the atmosphere. At the end point of the chemical at which it has been fully consumed, the cartridge including the battery is disposed of and the apparatus is reused on loading with a new cartridge.

In the conventional apparatus mentioned above, however, in which a cartridge is designed to be accommodated in the cylindrical housing of a given and limited size, the cartridge must be limited in size by the size of the cylindrical housing, and so must naturally be limited the battery in the number of battery cells and the chemical retainer (chemical accommodating receptacle) in size, too. The known apparatus has therefore been deficient for services of an extended time period and unsatisfactory if an increase in efficacy is sought.

Also, in the known apparatus, the power supply is disposed in a place where the airflow produced by the fan comes into contact with it. This battery arrangement thus creating a resistance to the blowing airflow has had the inconvenience that it makes the chemical volatilized, and diffused inefficiently.

It is accordingly a first object of the present invention with the above taken into account to provide a fan type chemical diffusing apparatus that comprises an apparatus main body, a chemical receptacle and an power supply housing which are made independent in volume (size) from one another to permit their respective variations in volume to be prepared based on its single basic design and selectively combined one with another, thereby making it possible to easily produce variations of the fan type chemical volatilizing and diffusing apparatus of the common design that vary in the amount of the chemical contained and the length of the time period with respect to the airflow amount by the fan for each service cycle while solving the abovementioned problems met in the prior art.

Also, the conventional chemical receptacle includes a receptacle main body having a cylindrical wall whose one end is closed with an end wall formed with a large number of vent holes and a cap body having a cylindrical wall whose one end is closed with an end wall formed with a large number of vent holes. The receptacle main and cap bodies are brought together to form the chemical receptacle by fitting the cylindrical wall of the cap body over an outer surface of the cylindrical wall of the receptacle main body and thereby the outer end surface of the cylindrical wall of the main body is against the inner surface of the end wall of the cap body.

Such a conventional chemical receptacle has the problem that when the receptacle main body is loaded from its open top with a chemical impregnated body such as a mass of beads impregnated with a chemical so they rise slightly above its brim and then the cap body is fitted over the main body, a faction of the chemical impregnated particles tends to be pinched between the outer end surface of the cylindrical wall of the main body and the inner surface of the end wall of the cap body, which prevents the cap body from tightly fitting with the receptacle main body.

Also, since the pinched chemical impregnated particles are not exposed to the airflow passing through the chemical receptacle, the chemical impregnated into these particles is hindered from volatilization and thus becomes useless.

Also, having axially opposite portions not identical in form, the conventional chemical receptacle when slide-fitted to the chemical receptacle retaining portion of the power supply housing can be fitted only from one side and cannot be fitted from the other side; hence hard to assemble.

It is therefore a second object of the present invention with the above taken into account to provide a chemical receptacle for a fan type chemical volatilizing and diffusing apparatus in which the chemical impregnated particles are kept from getting into an interstice between the receptacle main body and the cap body, and has its axially opposite portions made identical in the shape which either can be fitted to the chemical receptacle retaining portion, thereby facilitating its assembling.

Also, the conventional fan type chemical diffusing apparatus is commonly provided on its outer wall with a clip type fastener formed of an elastically deformable, tongue leaf like clip. This clip has its root portion attached and united to a support mount formed on the outer wall side of the apparatus main body in an insertion assembling method or the like. As its shape is viewed from its side, this clip has an area near its root portion that is the most spaced from the outer wall of the apparatus main body, an intermediate portion extending from that area towards its end portion and the most approaching the outer wall to provide a pressure foot portion for the clip, and the end portion where it leaps away from the outer wall, describing a circular arc. And, fitting the clip onto such an object as the hem of a pocket of the upper wear or the waist belt causes the object to be inserted and caught between the clip's pressure foot portion and the outer wall of the fan type chemical diffusing apparatus, and thereby this portable apparatus to be fastened and suspended.

By the way, with a conventional clip type fastening device as described above, the inconvenience has so far been met that the apparatus fastened tends to slip off the object to fall down while the user is at work. This has been found to be by reason of the fact that the surface of the wall to which the clip's pressure foot portion opposes is flat. Then, the force of the clip which effectively exerts to grip the object acts only on the space between the clip's pressure foot portion and the outer wall and, even if the gap between them is assumed to be zero, the force is limited only on the area lying between them. Then, if the object caught between them is so thin as the hem of a pocket, the force to grip it would be too weak to firmly fasten the apparatus of some weight to such an object from which it is suspended.

On the other hand, a thick wear or a waist belt as the object gripped which gives greater deformation to the clip provides greater force to grip therefor without the above inconvenience but, if the object is of a slippy material, the flatness of the surface of the outer wall as its counterpart inconveniently tends to cause the object to slip off the clip and the apparatus here again tends to slip off the object to fall.

While it is possible to increase the force to grip by the pressure foot portion by incorporating the clip into the support mount on the apparatus main body so that the pressure foot portion is held in elastic contact with the outerwall surface under a given pressure, this measure inconveniently not only complicates assembling the clip with the apparatus main body but also poses a problem of strength on the clip by the fact that a large force constantly is left to act on its root portion.

It is therefore a third object of the present invention to eliminate these inconvenience met in the prior art, and to provide a clip type fastening device that can be fastened to an object, regardless of whether it is thin or thick while holding the object caught thereby.

BRIEF SUMMARY OF THE INVENTION

In order to achieve the first object mentioned above, there is provided in accordance with the present invention in one aspect thereof a fan type chemical diffusing apparatus, characterized in that it comprises: an apparatus main body including a fan for producing an airflow, a motor for driving the fan and an airflow orifice through which the airflow produced by the fan passes; a chemical receptacle for accommodating a chemical impregnated body therein that is impregnated with a chemical, the chemical receptacle having vent holes; and a power supply housing for receiving a power supply therein, the power supply powering the motor, wherein the chemical receptacle and the power supply housing are adapted to be detachably loaded in the said apparatus main body and when loaded are each positioned therein so as to receive essentially no limitation in volume from the other.

This feature of the invention permits an apparatus main body, a power supply housing and a chemical receptacle which are independent of each other in volume (size) to be adopted. Variations different in volume of the apparatus main body, the power supply housing and the chemical receptacles may be prepared and selectively used or combined to enable variations different in size of the fan and motor (blower) to be adopted and various settings such as changes in the amount of a chemical and adjustments of the time period for services of the apparatus to be easily accomplished depending on particular places in which the apparatus is used. The above feature also permits the chemical receptacle alone to be exchanged when the chemical therein has been depleted.

According to one specific feature of the present invention in this aspect, the fan type chemical diffusing apparatus described above is characterized in that it further comprises a chemical receptacle retainer for holding the said chemical receptacle therewith and a cartridge made of the chemical receptacle retainer and the power supply housing made integral with each other, the cartridge being adapted to be disengageably inserted into and engaged with, and thereby loaded in, the apparatus main body.

This specific feature of the invention permits a cartridge made of the chemical receptacle retainer and the power supply housing made unitary to be detachably loaded into the apparatus main body. Therefore, when a battery used for the power supply has been exhausted and/or when the chemical has been depleted, exchanging the cartridge as a whole alone for the apparatus main body renders the apparatus reusable immediately, conveniently.

According to another specific feature of the present invention in this aspect, the fan type chemical diffusing apparatus described above is characterized in that it further comprises a chemical receptacle retainer for holding the chemical receptacle therewith, the chemical receptacle retainer and the power supply housing being adapted to be disengageably inserted into and engaged with, and thereby loaded, in the apparatus main body separately from each other.

This specific feature of the invention permits the chemical receptacle retainer to be detachably loaded into the apparatus main body and the power supply housing to be detachably loaded into the apparatus main body as well. Therefore, when a battery used for the power supply has been exhausted and/or when the chemical has been depleted, merely exchanging the chemical receptacle retainer and/or the power supply housing for the apparatus main body renders the apparatus reusable immediately, conveniently. Also, for example, if the power supply is of a commercial electric power, it becomes possible to exchange the chemical receptacle alone upon unloading the chemical receptacle retainer alone from the apparatus main body.

According to another specific feature of the present invention in this aspect, the fan type chemical diffusing apparatus described above is characterized in that the chemical receptacle is made integral with the chemical receptacle retainer.

This specific feature of the invention provides economical advantages for the process of forming or molding them. Also, the time and labor that need to be expended to load the chemical receptacle into the chemical receptacle retainer can advantageously be saved.

According to another specific feature of the present invention in this aspect, the fan type chemical diffusing apparatus described above is characterized in that the said apparatus main body further includes a switch for turning on and off current conduction to the said motor, and a pilot lamp for indicating or ascertaining this current conduction.

This specific feature of the invention of providing a switch and a pilot lamp on the side of the apparatus main body prevents disposal of the cartridge from causing disposal of the switch and pilot lamp together with the cartridge, resulting in no waste.

According to another specific feature of the present invention in this aspect, the fan type chemical diffusing apparatus described above is characterized in that the apparatus main body further includes an electric connector which when the power supply housing is loaded into the apparatus main body is brought into contact with the power supply received in the power supply housing to establish electric connection between the power supply and the switch.

This specific feature of the invention prevents the mistaken use or misuse because it is ensured that turning ON the switch on the apparatus main body by itself does not drive the fan.

According to another specific feature of the present invention in this aspect, the fan type chemical diffusing apparatus described above is characterized in that the airflow opening is disposed in a side face of the apparatus main body.

This specific feature of the invention permits the apparatus when used hung on a strap, suspended from the shoulder or fastened on the waist belt to produce an chemical entrained airflow that runs out of its side face sideways and to stream as it wraps the user's body, thereby enhancing the chemical's efficacy to around the body.

According to another specific feature of the present invention in this aspect, the fan type chemical diffusing apparatus described above is characterized in that the apparatus main body further includes an unloading means for releasing the insertion engagement of said power supply housing and/or the chemical receptacle retainer with the apparatus main body.

This specific feature of the invention prevents the cartridge from detaching from the apparatus main body unless the unloading means is acted on to release its insertion engagement. It prevents the cartridge in the apparatus used, for example, as suspended from the shoulder of the user in a fieldwork from going astray. Also, providing an unloading or engagement release button on the side of the apparatus main body allows the unloading means to be repetitively used if the cartridge is discarded.

According to another specific feature of the present invention in this aspect, the fan type chemical diffusing apparatus described above is characterized in that the apparatus further comprises a member attached to a rear surface of the apparatus main body for having the apparatus main body suspended from, or fixed fast to, another body or object.

This specific feature of the invention permits the apparatus to be used as hung on a strap, suspended from the shoulder or fastened on the waist belt. It also permits the apparatus if used as fixed fast to another object or article to be freed from a risk of tumbling or the like.

According to another specific feature of the present invention in this aspect, the fan type chemical diffusing apparatus described above is characterized in that the power supply housing is provided with a power supply accommodating section that is so positioned as not to be contacted by the fan produced airflow passing through the chemical receptacle.

This specific feature of the invention prevents a battery as the power supply from being exposed to contamination such as corrosion by a chemical entrained airflow.

According to another specific feature of the present invention in this aspect, the fan type chemical diffusing apparatus described above is characterized in that the power supply is constituted by a battery.

This specific feature of the present invention of making use of a battery for the power supply enables the power supply housing to be exchanged as a cartridge and also allows the apparatus to be made portable and to be serviced in a place such as a field where no commercial power supply is available.

According to another specific feature of the present invention in this aspect, the fan type chemical diffusing apparatus described above is characterized in that the battery when accommodated in the power supply housing is partially exposed to its outside.

This specific feature of the invention enables the presence of a battery as the power supply to be easily ascertained.

According to another specific feature of the present invention in this aspect, the fan type chemical diffusing apparatus described above is characterized in that the power supply housing is adapted to accommodate a battery case therein for the battery, the battery case being receivable as a drawer in the power supply housing.

This specific feature of the invention facilitates loading and unloading a battery as the power supply and makes it easy to maintain and exchange the power supply.

According to another specific feature of the present invention in this aspect, the fan type chemical diffusing apparatus described above is characterized in that the power supply housing is adapted to accommodate a battery case therein for the battery, the battery case has a cut-out formed therein for permitting an electric connector disposed in the apparatus main body to contact a battery terminal in the battery case.

This specific feature of the invention allows the electrical connection that is needed for the operation of the apparatus to be completed simply by merely loading the apparatus main body with a cartridge.

According to another specific feature of the present invention in this aspect, the fan type chemical diffusing apparatus described above is characterized in that the battery has an exhaustion point that is made coincident with an end point in depletion of the chemical.

This specific feature of the invention permits the chemical in the chemical receptacle to have been used up when the battery is used up bringing the fan to a halt. Then, both can be exchanged at the same time, thereby facilitating maintenance of the apparatus.

According to another specific feature of the present invention in this aspect, the fan type chemical diffusing apparatus described above is characterized in that the power supply housing and/or the chemical receptacle retainer are/is adapted to be loaded into the apparatus main body by sliding the former into the latter for engagement therewith by means of a slide system.

According to another specific feature of the present invention in this aspect, the fan type chemical diffusing apparatus described above is characterized in that the slide system whereby the power supply housing and/or the chemical receptacle retainer are/is slid into the apparatus main body for engagement therewith includes: a pair of slide engagement members provided at opposite sides of the power supply housing and/or the chemical receptacle retainer along a direction in which the power supply housing and/or the chemical receptacle retainer are/is slid into the apparatus main body; and a pair of their counterparts provided at opposite sides of the apparatus main body along the direction.

These specific features of the invention facilitate loading the apparatus main body with the power supply housing.

According to another specific feature of the present invention in this aspect, the fan type chemical diffusing apparatus described above is characterized in that the pilot lamp provided in the apparatus main body is constituted with a light emitting diode.

This specific feature of the invention of using a light emitting diode for the pilot lamp saves energy consumption for the power supply (battery).

According to another specific feature of the present invention in this aspect, the fan type chemical diffusing apparatus described above is characterized in that the chemical receptacle is adapted to be detachably loaded into the chemical receptacle retainer from its outside.

This specific feature of the invention of enabling the chemical receptacle to be detachably inserted into the chemical receptacle retainer from its outside facilitates exchanging the chemical receptacle with respect to the apparatus.

According to another specific feature of the present invention in this aspect, the fan type chemical diffusing apparatus described above is characterized in that it further comprises hood means for covering, respectively, an airflow opening formed in the apparatus main body, and vent holes formed in the chemical receptacle retainer and open to its outside or an exposed region of the chemical receptacle when held by the chemical receptacle retainer.

This specific feature of the invention prevents rainwater from getting in the outer airflow opening or a region of the chemical receptacle that projects from the apparatus.

According to another specific feature of the present invention in this aspect, the fan type chemical diffusing apparatus described above is characterized in that the said fan is adapted to send the airflow towards the chemical receptacle, and a heater means is disposed between the chemical receptacle and the fan.

This specific feature of the invention of enabling the airflow passing through the chemical receptacle to be warmed makes it possible to volatilize the chemical well from a chemical impregnated body in the chemical receptacle.

According to another specific feature of the present invention in this aspect, the fan type chemical diffusing apparatus described above is characterized in that the chemical receptacle is constituted by a first chemical receptacle adapted to be so held by the chemical receptacle retainer that its one end face lies outside of the chemical receptacle retainer, the apparatus further comprising a coupling means for coupling a second chemical receptacle to that end face of the first chemical receptacle.

According to another specific feature of the present invention in this aspect, the fan type chemical diffusing apparatus described above is characterized in that the chemical receptacle has its volume variable.

These specific features of the invention of enabling the chemical receptacle that is loaded in the apparatus to be varied in capacity makes it possible to change the apparatus's serviceable time period or to provide variations of the apparatus varied in serviceable time period.

According to another specific feature of the present invention in this aspect, the fan type chemical diffusing apparatus described above is characterized in that the chemical receptacle is fitted on one end face thereof with a shutter for controlling the rate of flow of air passing through the chemical receptacle.

This specific feature of the invention of enabling the rate of airflow through the chemical receptacle to be controlled permits the rate of diffusion of the chemical therefrom to be changed.

According to another specific feature of the present invention in this aspect, the fan type chemical diffusing apparatus described above is characterized in that it further comprises a timer incorporated in the said apparatus main body for establishing a time period of operation of the said motor.

This specific feature of the present invention of enabling a timer to be installed and preset eliminates the need to turn ON and OFF the switch, and permits the user to preset the time period as it likes, to prevent the user from forgetting to switch off, resulting in no waste.

In order to achieve the aforementioned second object, there is also provided in accordance with the present invention in a second aspect thereof a chemical receptacle for use with a fan type chemical diffusing apparatus for diffusing a chemical in a chemical impregnated body accommodated in the chemical receptacle by means of an airflow produced by a fan, characterized in that it comprises: a cylindrical receptacle main body having its cylindrical wall closed with its one end wall formed with a large number of vent holes; and a cylindrical lid body having its cylindrical wall closed with its one end wall formed with a large number of vent holes, wherein the cylindrical wall of the said lid body is adapted to be fitted into and with an inner surface of the cylindrical wall of the receptacle main body.

This specific feature of the invention that enables the cylindrical wall of the lid body when loaded into the receptacle main body to be fitted into the inside of the cylindrical wall of the receptacle main body, causes the chemical impregnated particles which are located in contact with the inner surface of the cylindrical wall in the receptacle main body to be forced aside into the interior of the receptacle main body by the cylindrical wall of the lid member. As a result, there is produced no pinch of these particles between an end face of the receptacle main body and an end wall of the lid body.

According to a specific feature in this second aspect of the present invention, the chemical receptacle described above is characterized in that it has its axially opposite side portions identical in the shape.

This specific feature of the invention that makes the chemical receptacle have its axially opposite side portions identical in the shape enables the chemical receptacle to be loaded into the chemical receptacle retaining section from either side and facilitates its assembling. Also, the lid body fitted into the receptacle main body has no external projection. Providing no hook for fingers, therefore, the lid body is made hard to be removed from the receptacle main body by, e.g., an infant, and makes the chemical receptacle highly safe without the risk that the chemical impregnated body therein is touched.

In order to achieve the aforementioned third object, there is also provided in accordance with the present invention in a third aspect thereof a clip type fastening device for a fan type chemical diffusing apparatus, including a clip member in the form of a tongue attached to an outer wall of the fan type chemical diffusing apparatus wherein the clip having a pressure foot portion is adapted to be so hung on an object such as an apparel of the user that the object is inserted and gripped between the external wall of the fan type chemical diffusing apparatus and the pressure foot portion, thereby fastening the fan type chemical diffusing apparatus to the object, characterized in that the clip member comprises a plurality of clip pressure foot portions disposed mutually spaced apart in a direction perpendicular to that in which the object is inserted as aforesaid; and one or more raised portions so formed on the said outer wall as to come into between adjacent such pressure foot portions.

This feature in the third aspect of the invention enables an object such as the hem of an apparel's pocket when the clip member is hooked thereon to be gripped in a wavy form between the clip's pressure foot portions and the raised portion or portions from the outer wall of this portable apparatus interposed between these pressure foot portions. Therefore, the portable apparatus comes to be firmly fastened to the object even if it is a thin cloth. If the object is a thick cloth, deformation of the clip member in proportion to its thickness here makes its gripping force still larger.

Given the ability in this way to fix the clip member fast to the object such as a cloth, the fastening device according to this feature of the invention eliminates the need to bring any pressure foot preliminarily into pressure contact against the outer wall of the apparatus main body and to hold it pressured contacted therewith. Since the clip can be attached in its natural state, its assembling is made easier.

If the object to be caught is a solid such as a belt, then the object can be caught without any trouble by inserting the same into the clip member beyond its pressure foot portion full to its root portion. The object is led to enter up to the space defined with the raised portion or portions, thereby holding the apparatus fastened thereto without coming off.

According to a specific feature in the third aspect of the present invention, the fastening device described above is characterized in that at least one of an inner surface area of the pressure foot portion of the clip member, a surface area of the outer wall that opposes the inner surface area of the pressure foot portion and a surface area of a raised portion is made uneven to provide a slip resistance for the object.

This specific feature of the invention enables the object, regardless whether it is thin or thick, to be fastened to by contacting the portions made uneven to provide a slip resistance thereto.

According to another specific feature in the third aspect of the present invention, the fastening device described above is characterized in that the clip member has a root and an end portion which lie at a substantially equal height from the outer wall.

This feature of the invention enables this portable apparatus placed with the clip member facing down to be placed horizontally.

DETAILED DESCRIPTION

Figure 1:
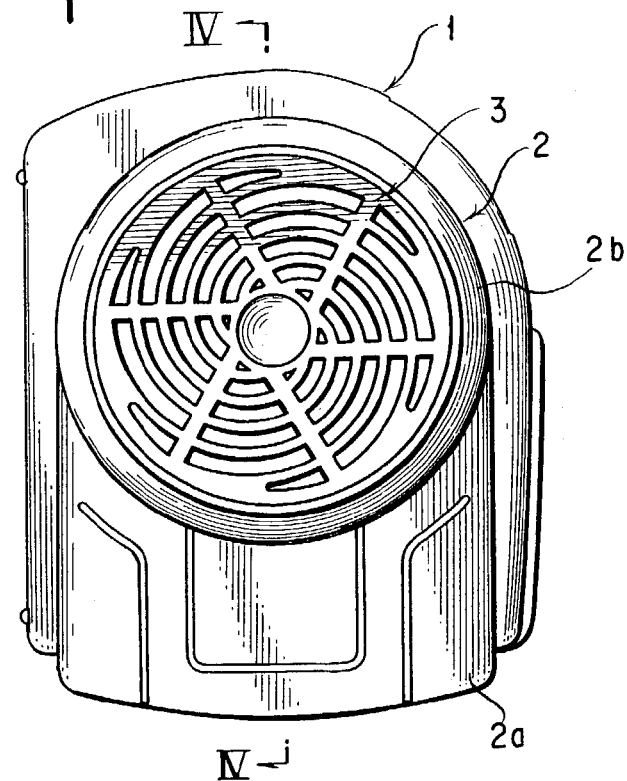
FIG. 1 is a front elevational view illustrating a fan type chemical diffusing apparatus that represents a first form of embodiment of the present invention.

An explanation is first given in respect of a fan type chemical diffusing apparatus according to the first form of embodiment of the present invention with reference to FIGS. 1 to 16. The apparatus is shown to comprise an apparatus main body 1, a cartridge 2 formed of a power supply housing 2a and a chemical receptacle retainer 2b which are united together, and a chemical receptacle 3. The chemical receptacle 3 here is adapted to be fitted into, held by and disengaged from a chemical receptacle retaining section 4 of the chemical receptacle retainer 2*b*. And, the cartridge 2 is adapted detachably to slide-fit with the apparatus main body 1. Namely, slidably inserted into the apparatus main body 1 in a direction perpendicular to the central axis of the chemical receptacle retaining section 4, the cartridge 2 is adapted to come into engagement with the apparatus main body 1. To detach the cartridge 2 or disengage it from the apparatus main body 1, an engagement releasing button 6 is provided.

Figure 4:
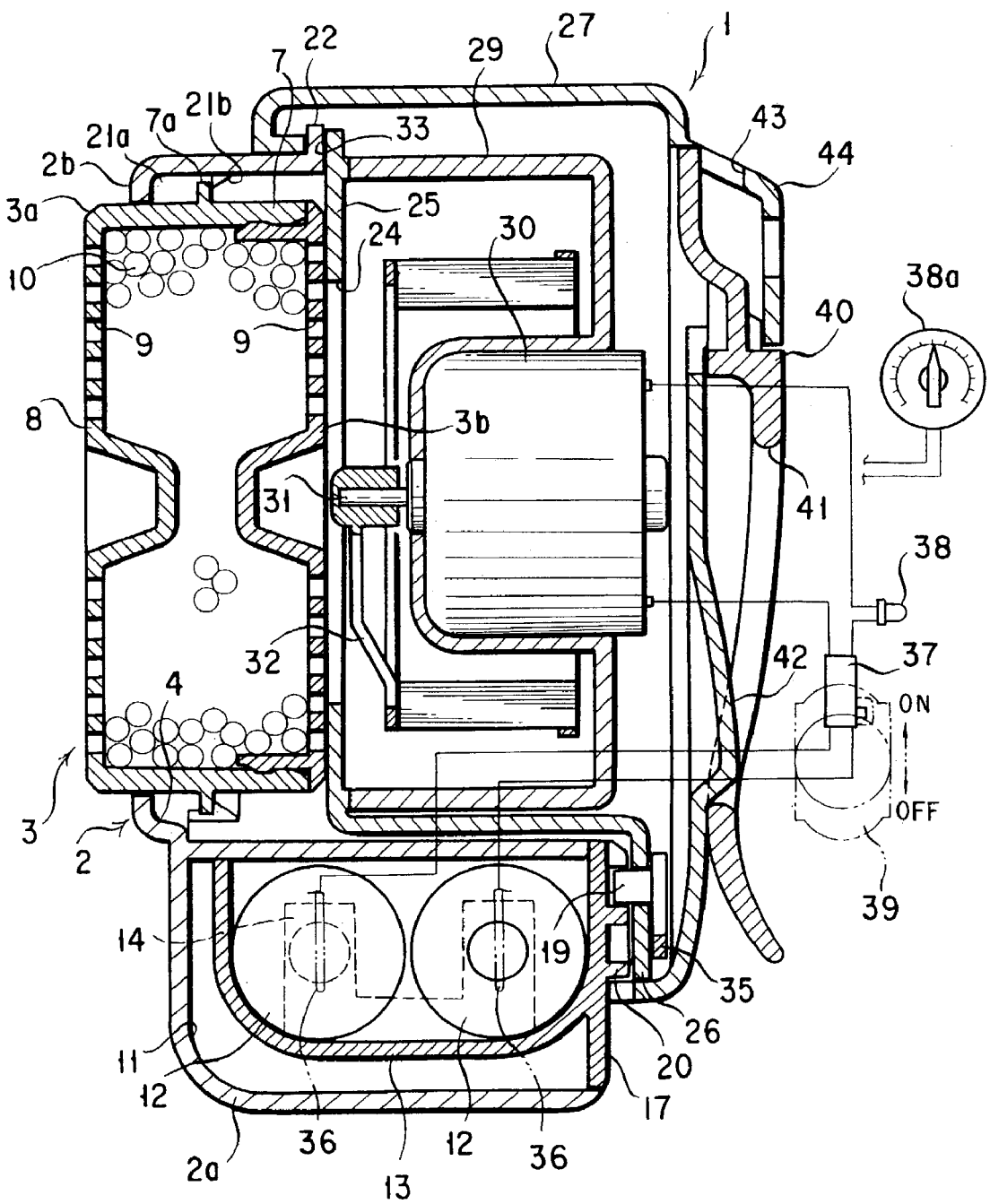
FIG. 4 is a side cross sectional view in elevation taken along the line IV-IV in FIG. 1 as viewed in the direction of the arrows.
Figure 5:
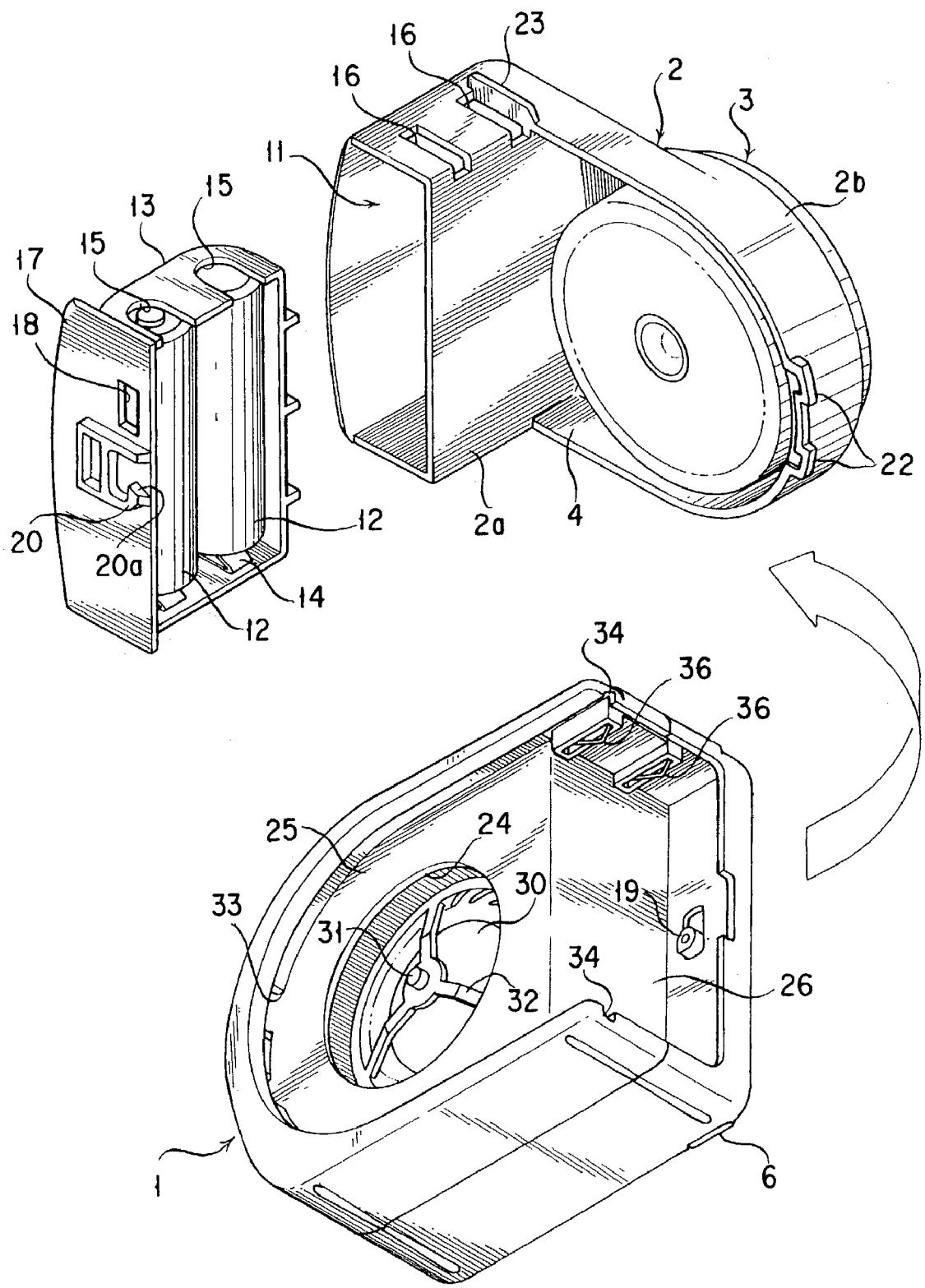
FIG. 5 is a decomposed perspective view of the apparatus shown in FIGS. 1 to 4.
Figure 6:
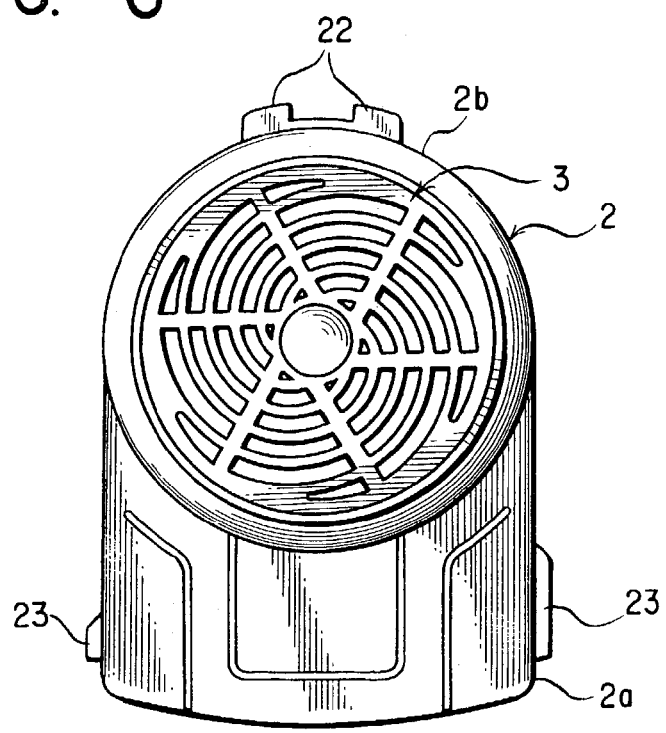
FIG. 6 is a front elevational view illustrating a cartridge for use in the apparatus shown in FIGS. 1 to 5.
Figure 7:
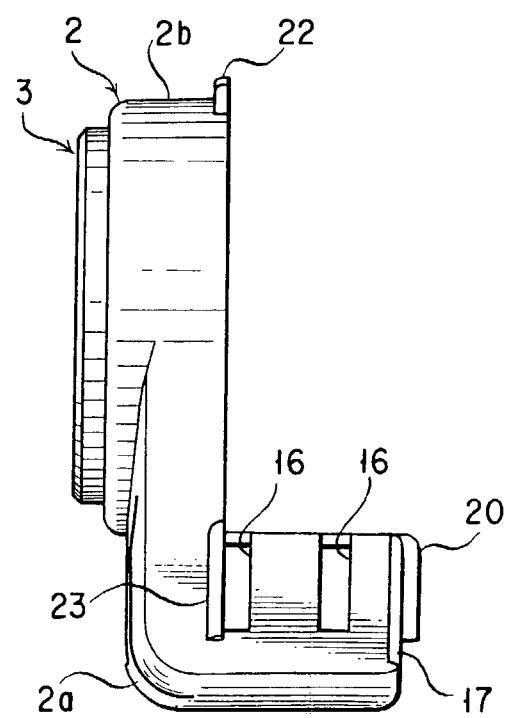
FIG. 7 is a side elevational view of the cartridge shown in FIG. 6.

The chemical receptacle 3 as shown in FIG. 4 comprises a receptacle main body 3*a* having a cylindrical wall 7 formed with an annular, projecting rim or flange 7*a* for engagement axially in its midway and of which one side is closed with an end wall 8 made continuous therewith, and a lid body 3*b* with which the other side, open end of the receptacle main body 3*a* is closed, wherein each of the end wall 8 and the lid body 3*b* has a large number of vent holes 9 formed therethrough. The total open surface area occupied by the respective vent holes through the end wall 8 and the lid body 3*b* is made at least 60% of the total surface area of the end wall 8. Accommodated within the chemical receptacle 3 is a chemical impregnated body 10, here in the form of a mass of beads or spherical particles impregnated with a chemical that as will be described later in detail is made capable of volatilization in air. Other than being a mass of beads or spherical particles, the chemical impregnated body 10 may be a mass of wire or wires or small pieces, or a honeycomb or sponge structure. They may be made of pulp, nonwoven fabric or woven fabric, synthetic resin or an inorganic substance such as silica gel.

Referring to FIGS. 4 to 8, the cartridge 2 which comprises the power supply housing 2*a* and the chemical receptacle retainer 2*b* is L-shaped in a side view. It has at its base portion a power supply accommodated section 11 formed in hollow with one end open. The power supply accommodating section 11 has a battery case 13 inserted therein as slidable in and out like a drawer, the battery case 13 as shown being capable of accommodating therein two battery cells 12 as the power supply for the apparatus.

The battery case 13 has in its interior at one axial end side of the battery cells 12 a connecting terminal 14 formed so as to electrically connect the positive terminal of one of the two battery cells 12 to the negative terminal of the other. The battery case 13 also has at its other end side a pair of cutouts 15 and 15 formed to expose the respective opposite terminals of these battery cells 12. On the other hand, the power supply housing 2*a* to be loaded with the battery case 13 has a pair of cutout openings 16 and 16 formed at positions beneath which the cutouts 15 and 15 are respectively arriving when the battery case 13 is fully inserted into the housing 2*a*. This arrangement enables those exposed terminals of the two battery cells 12 in the battery case 13 to be brought into contact with a corresponding pair of conducting members or electrical contacts 36 located outside of the power supply housing 2*a*.

The battery case 13 further has an opening or small window 18 formed through its outer wall 17 to enable the presence of the battery cells 12 inside to be checked. This outer wall 17 is also provided with a hook 20 with which an engagement protrusion piece 19 comes to disengageably engage when operated by the abovementioned release button 6.

Figure 8:
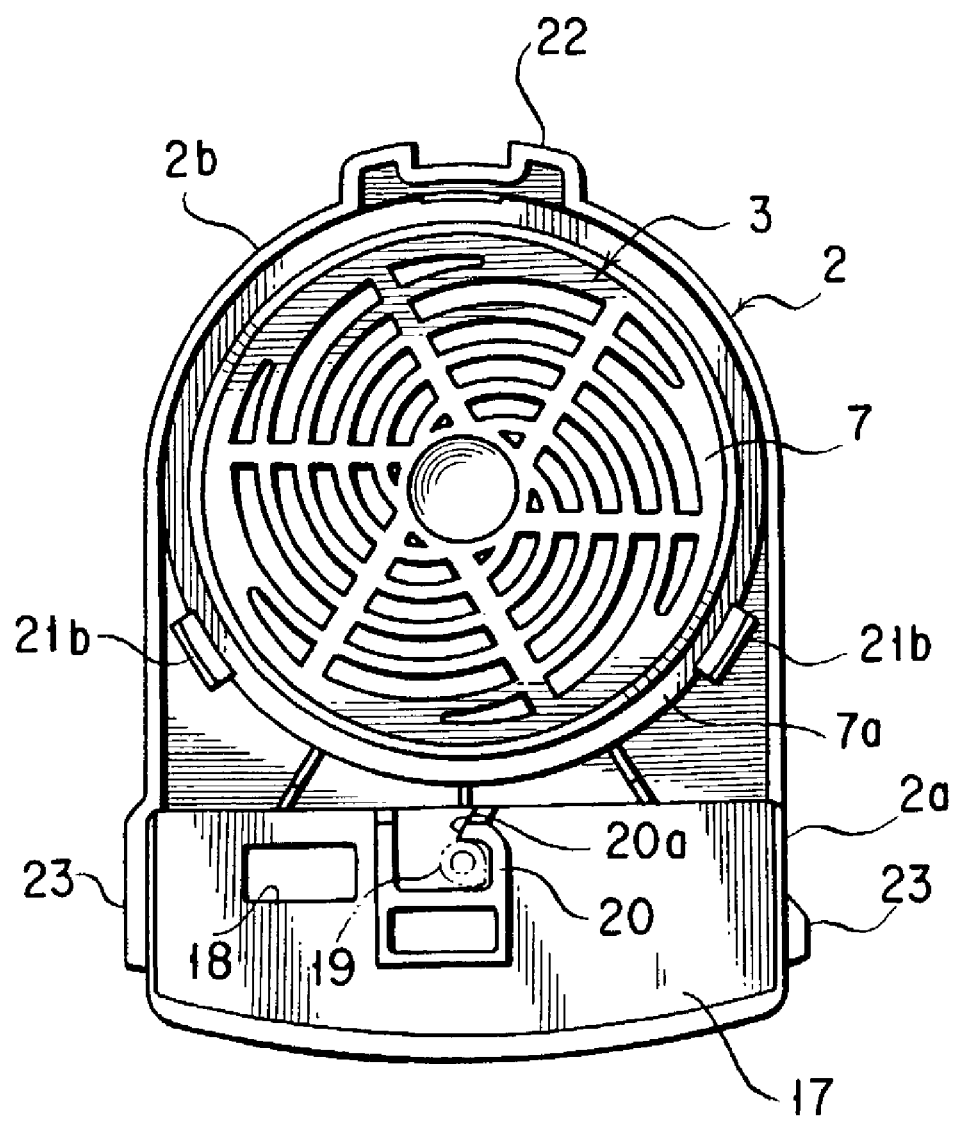
FIG. 8 is a rear elevational view of the cartridge shown in FIGS. 6 and 7.
Figure 9:
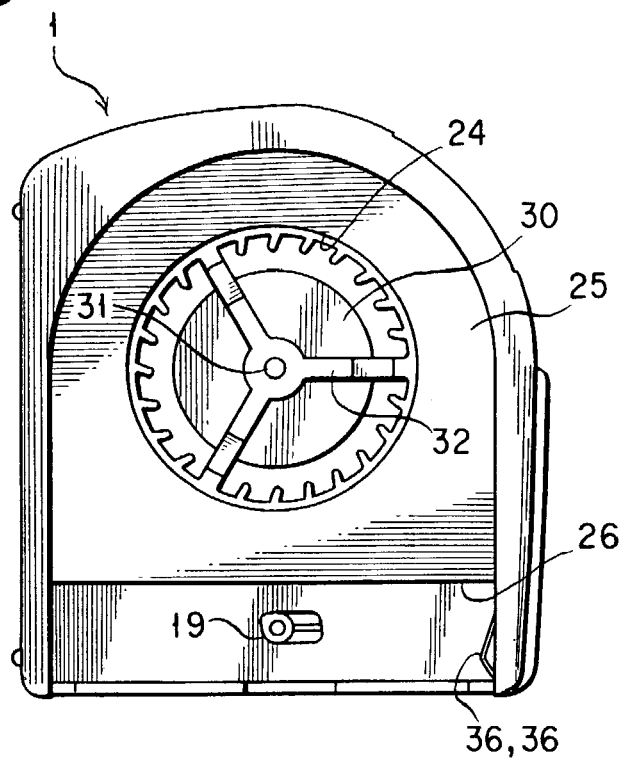
FIG. 9 is a front elevational view illustrating an apparatus main body alone of the apparatus shown in FIGS. 1 to 5.
Figure 10:
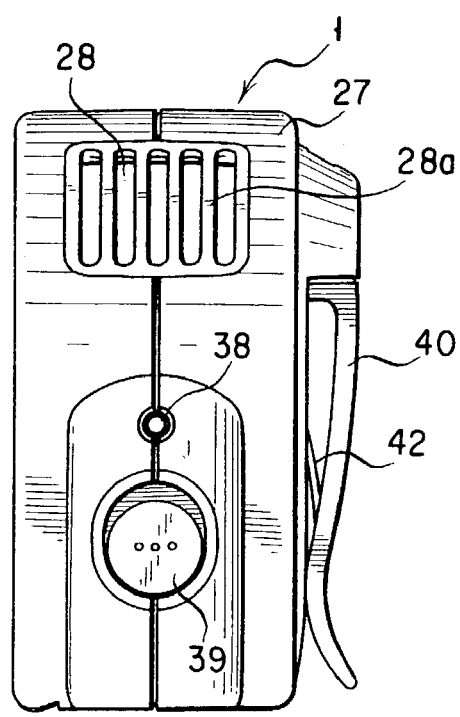
FIG. 10 is a side elevational view of the apparatus main body shown in FIGS. 1 to 5 and 9.

The chemical receptacle retainer 2*b* located above the power supply housing 2*a* and remote from the power supply accommodating section 11 is designed to hold the chemical receptacle 3 detachably in the chemical receptacle retaining section 4, which is formed open circular in the chemical receptacle retainer 2*b*. The chemical receptacle retaining section 4 is formed in its inner, annular surface with a first and a second set of projecting pieces 21*a* and 21*b*, outer and inner, which as can be seen from FIGS. 4 and 8 are designed to axially hold the circular, projecting engagement rim 7*a* on the chemical receptacle 3 inserted into the chemical receptacle retaining section 4 from its inner side. The inner, projecting pieces 21*b* temporarily deform when the projecting engagement rim 7*a* is led in and out past them and then return to their original shape. In this arrangement, therefore, carrying the projecting engagement rim 7*a* across the inner projecting pieces 21*b* outwards brings the chemical receptacle 3 into engagement with chemical receptacle retaining section 4 to be held thereby. Conversely, carrying the former 7*a* across the latter 21*b* inwards disengages the chemical receptacle 3 from its retaining section 4 inwards.

The cartridge 2 as will be seen from FIGS. 4 to 8 has its end (top) formed with a pair of engagement projections 22 and has its base laterally formed with a pair of rails 23 each along the direction in which the cartridge 2 is slid into the apparatus main body 1.

Mention is next made of the way in which the apparatus main body 1 is constructed.

Referring to FIGS. 4, 5, 9, 10 and 11, the apparatus main body 1 as the counterpart of the cartridge 2 to establish a slide fit therewith, includes, its outer wall 27, an upper inner wall 25 which opposing the chemical receptacle retaining section 4 in the cartridge 2, is formed with an inner airflow opening 24 that opposes the chemical receptacle 3 held by the chemical receptacle retaining section 4, and a lower inner wall 26 that opposes the base of the power supply housing 2*a*. Provided in the space between these inner walls 25 and 26 and the outer wall 27 is a spiral duct 29 that communicates a region of the inner airflow opening 24 with an outer airflow opening 28. And, within this duct 29 is there mounted a silocco fan 32 having a region of its central axis fronting the inner airflow opening 24, the silocco fan 32 being coupled to the output shaft 31 of a motor 30 supported to lie in a region of the center of the duct 29 as shown also in FIG. 11. The outer airflow opening 28 is formed in a side face of the outer wall 27 and is made open so that it faces in a direction essentially perpendicular to that in which the inner airflow opening 24 faces, thereby permitting the airflow produced by the fan 32 to be discharged sideways of the apparatus main body 1.

The apparatus main body 1 has a pair of engagement holes 33 formed at its inner top, with which the two engagement projections 22 formed on the top of the cartridge 2 are designed to engage, respectively. It also has a pair of grooves 34 and 34 formed in its inner bottom, two opposed surfaces, with which the two rails 23 and 23 formed on the cartridge 2 are designed to engage, respectively.

Figure 11:
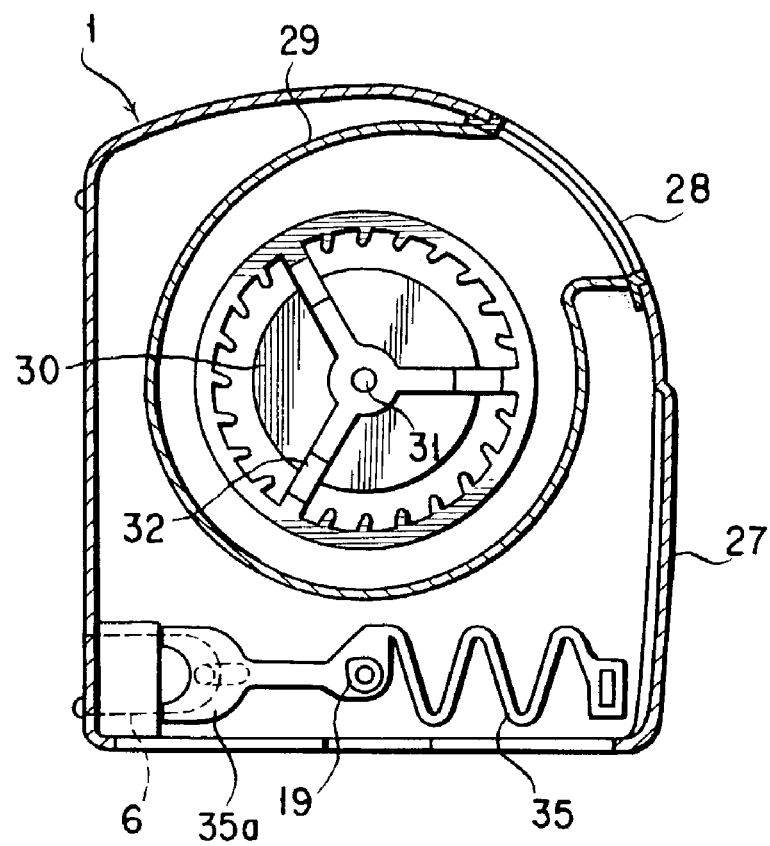
FIG. 11 is a cross sectional view in elevation illustrating the interior of the apparatus main body shown in FIGS. 1 to 5, 9 and 10.

With continued reference with FIGS. 4, 5, 8 and 11, in the apparatus main body 1 the engagement protrusion piece 19 mentioned above is also internally equipped which with the cartridge 2 brought into engagement with the apparatus main body 1 is designed to engage with the hook 20 formed on the battery case 13. This engagement protrusion piece 19 is so internally equipped as to be movable sideways by means of a spring 35 made integrally with its body portion from a plastic, within the apparatus main body 1. The body portion of the engagement protrusion piece 19 as shown in FIG. 11 is coupled, at its end 35*a* opposed to the spring 35 in the direction of its sideway movement, to the engagement releasing button 6 that is slidably mounted on the outer wall 27 of the apparatus main body 1.

Mounted to one inner, lower side face of the apparatus main body 1 in those areas corresponding in position to the cutouts 16 and 16 formed in the power supply housing 2a is a pair of electric contacts 36 and 36 which are admitted into the battery case 13 through these cutouts 16 and 16 to contact the terminals of the battery cells 12, respectively. These electric contacts 36 and 36 are each made of a wire that is elastic, and are electrically connected to the motor 30 via an ON/OFF switch 37 included the outer wall 27 of the apparatus main body 1. In its switching circuit is there a pilot lamp 38 connected that lights up when the switch 37 is turned ON. This switching circuit may also have a timer 38a connected in series with the switch 37. The switch 37 is here designed to be turned ON and OFF by means of a slide piece 39 exposed from the outer wall 27.

Figure 2:
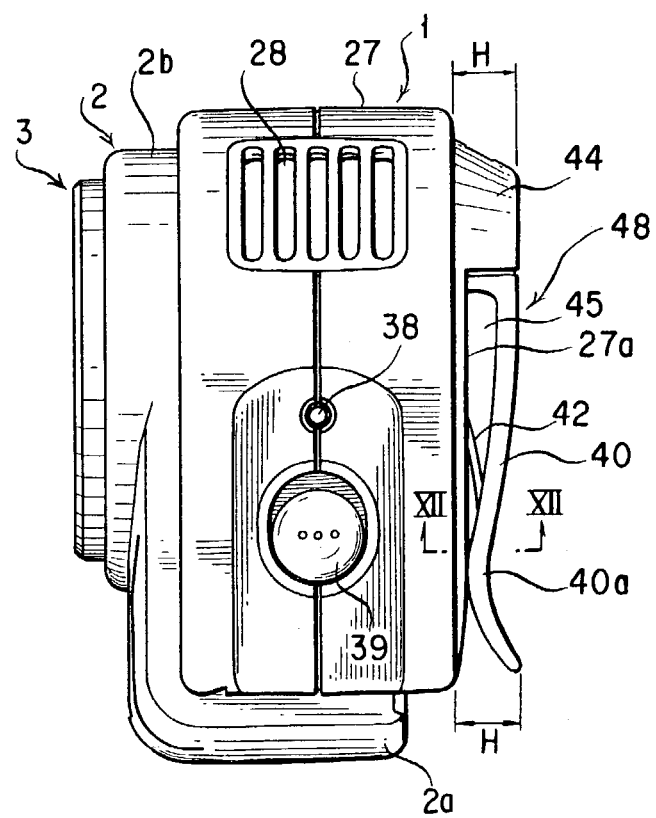
FIG. 2 is a side elevational view of the apparatus shown in FIG. 1.
Figure 3:
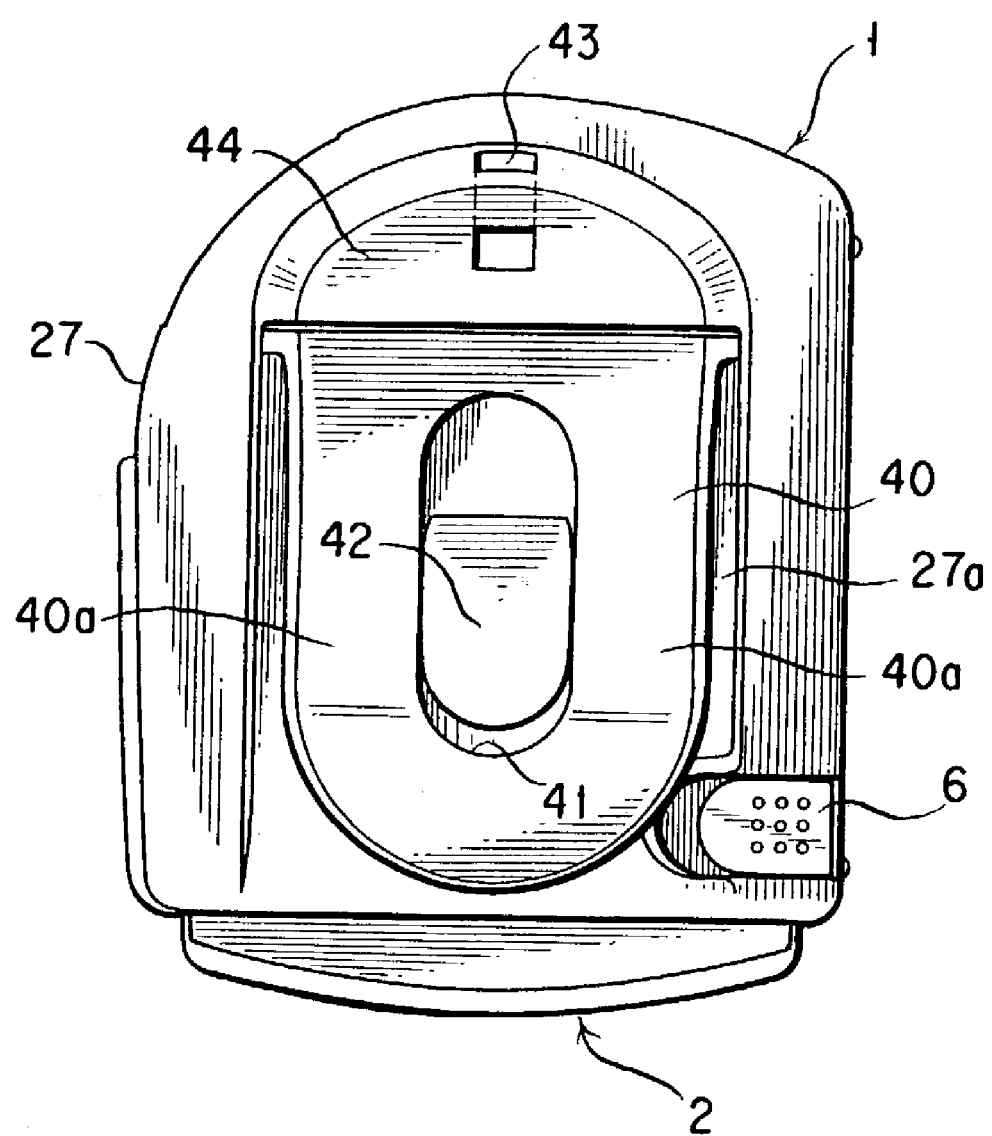
FIG. 3 is a rear elevational view of the apparatus shown in FIGS. 1 and 2.

Referring to FIGS. 2, 3 and 4, this fan type chemical diffusing apparatus is provided therefor with a clipping device or clip fastener 48 on the rear 27a of the outer wall 27 of the apparatus main body 1. The clip fastener 48, i.e., a device for fastening by a clip the apparatus to an object such as an apparel of the user comprises a clip 40 having a hole 41 and deformably fastened to the rear surface 27a of the outer wall 27 of the apparatus main body 1, and a raised portion or projection 42 formed to rise from the rear surface 27a of the outer wall 27 and adapted to enter the hole 41 in the clip 40.

The clip 40 is made in the form of a tongue and has its root portion joined to a supporting mount 44 joined to the rear surface 27a of the outerwall 27 of the apparatus main body, both unitarily by an integrated assembling method. And, as the clip 40 is viewed laterally, it is configured to be spaced from the rear wall surface 27a in a region near the root portion. Then, the clip 40 in an area closer to its end a little towards the root portion becomes closest to the rear wall surface 27a to provide a pressure foot 40a therefor and in an area from the pressure foot portion 40a to the end leaps away from the rear wall surface 27a, describing a circular arc.

Because of the hole 41 formed in the clip 40, two or a pair of such pressure foots 40a are created at the opposite sides of the hole 41, respectively, namely placed in a line perpendicular to the direction in which the clip 40 is inserted with. And, it is between these pressure foots 40a that the projection 42 that enters this hole 41 is formed on the rear surface 27a of the outer wall 27. This projection 42 as viewed laterally is formed to intersect the pressure foots 40a, and a space 45 is made up in a region between the root portion of the clip 40 and the rear wall surface 27a.

The supporting mount 44 to which the root portion of the clip 40 is fastened in flush therewith and the end of the clip 40 are arranged to lie at the same height H from the rear surface 27a of the outer wall 27.

The supporting mount 44 is provided at its center with a strap threading hole 43 through which a strap is threaded.

Figure 12:
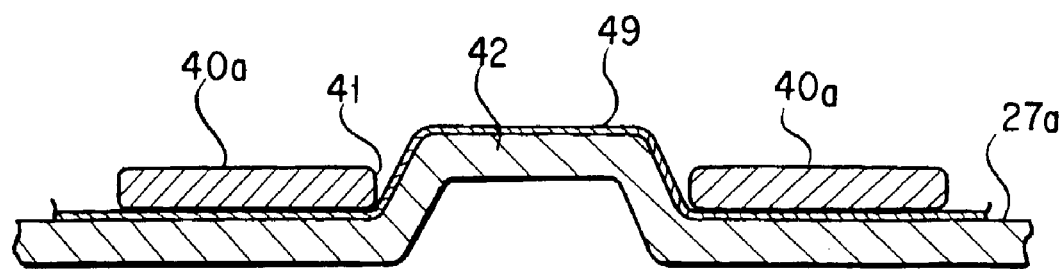
FIG. 12 is a cross sectional view in plan taken along the line XII-XII in FIG. 2 as viewed in the direction of the arrows.

With the clip device 48 so constructed as mentioned above, hooking the clip 40 on the hem of a pocket on the upper wear allows this hem 49 of pocket as shown in FIG. 12 to be inserted into the space between the clip 40 and the rear surface 27a of the outer wall 27. Then, the pocket hem 49 is pressed down or against the rear wall surface 27a with the pressure foots 40a and 40a located at the opposite sides of the hole 41 in the clip and pressed up in the hole 41, off the pressure foots 40a and 40a, with the projection 42, thereby held down and gripped in a wavy pattern.

As a result, even if an object to be gripped on and fastened to is a thin one such as the pocket hem 49, the fan type chemical volatilizing and diffusing apparatus is firmly caught on and fastened to it. On the other hand, a thick object being the case will cause the clip 40 to deform in proportion to its thickness and the space between the clip 40 and the rear surface 27a to be forced to widen. This makes even greater the spring pressure applied on it than on the thin object, thereby fastening the apparatus even more firmly thereto.

Further, with the object to be caught by the clip being a waist belt, the belt will be caught in the space 45 between a region of the root portion of the clip 40 and the rear surface 27a of the outer wall 27, thereby holding the apparatus fastened thereto without falling off.

The feature that the supporting mount 44 and the clip 40 are made even in height from the support surface 27a enables an object to be smoothly inserted between the clip 40 and the support surface 27a. The feature also enables the fan type chemical volatilizing and diffusing apparatus to be horizontally placed such as on a table by simply placing the apparatus with the clip 40 facing down.

In the form of embodiment described above, it is also possible to configure the clip 40 with a number of pressure foot portions 40a spaced apart from one another in the form of the teeth of a comb and a number of projections 42 each designed to enter between adjacent such pressure foot portions 40a as mounted on the rear support surface 27a of the outer wall 27 of the apparatus main body.

In the form of embodiment described above, at least of one of an inner surface area of the pressure foot portion 40a of the clip 40, a surface area of the outer wall 27 that opposes the inner surface area of the pressure foot portion 40a and a surface area of the raised portion 42 is made uneven to provide a slip resistance for the object. The uneven portion may be made of a plurality of raised streaks, a large number of punctate projections or an uneven surface having a slip resistance.

An explanation in detail is next given in respect of the chemical receptacle 3 with reference to FIGS. 13 to 16.

Figure 15A:
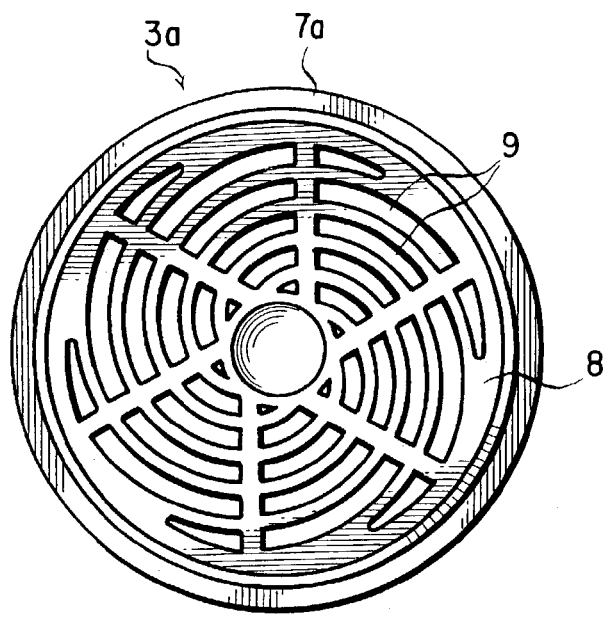
FIGS. 15A and 15B are a front elevational view and a side cross sectional view in elevation, respectively, illustrating a receptacle main body of the chemical receptacle shown in FIGS. 13 and 14.
Figure 15B:
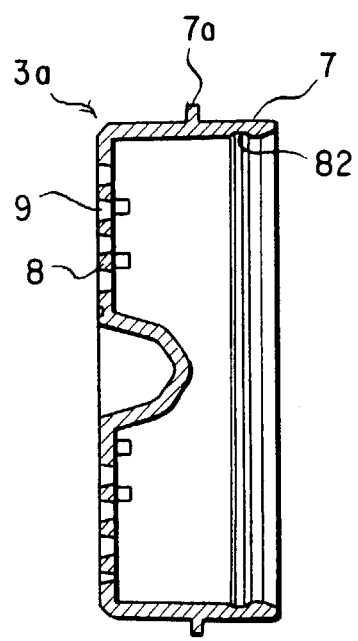
Figure 16A:
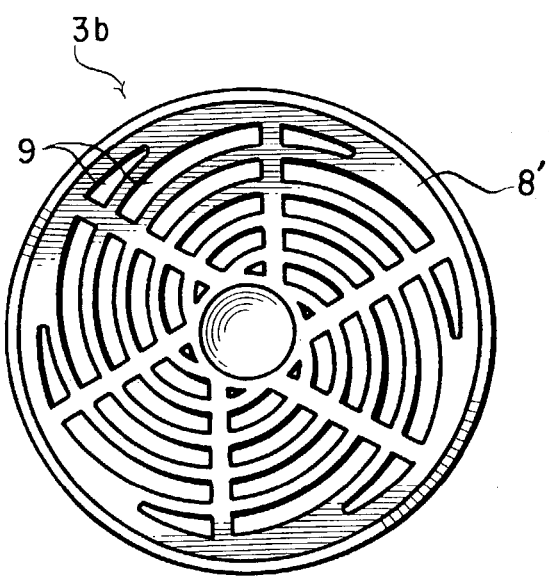
FIGS. 16A and 16B are a front elevational view and a side cross sectional view in elevation, respectively, illustrating a lid body for the chemical receptacle shown in FIGS. 13 and 14.
Figure 16B:
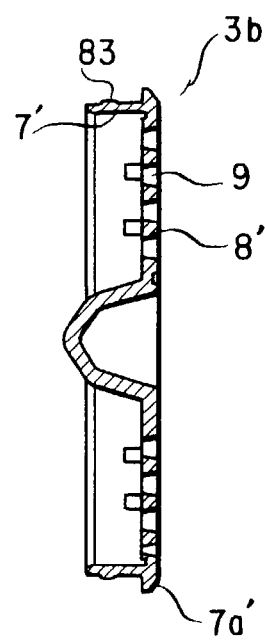

The chemical receptacle 3 as shown in FIGS. 15A and 15B includes a receptacle main body 3a formed of a cylindrical wall 7 having its one end closed with an end wall 8 formed with a large number of vent holes 9. The chemical receptacle 3 as shown in FIGS. 16A and 16B also includes a lid body 3b formed of a cylindrical wall 7' having its one end closed with an end wall 8' formed with such vent holes 9.

Here, the cylindrical wall 7' of the lid body 3b has an outer diameter such that the cylindrical wall 7' is closely fitted in the cylindrical wall 7 of the receptacle main body 3a as received by its inner surface. Further, the end wall 8' of the lid body 3b is larger in diameter than the cylindrical wall 7' so that its periphery provides a flange 7a' for the cylindrical wall 7'. The flange 7a' is made substantially equal in outer diameter to the cylindrical wall 7 of the receptacle main body 3a.

Figure 13:
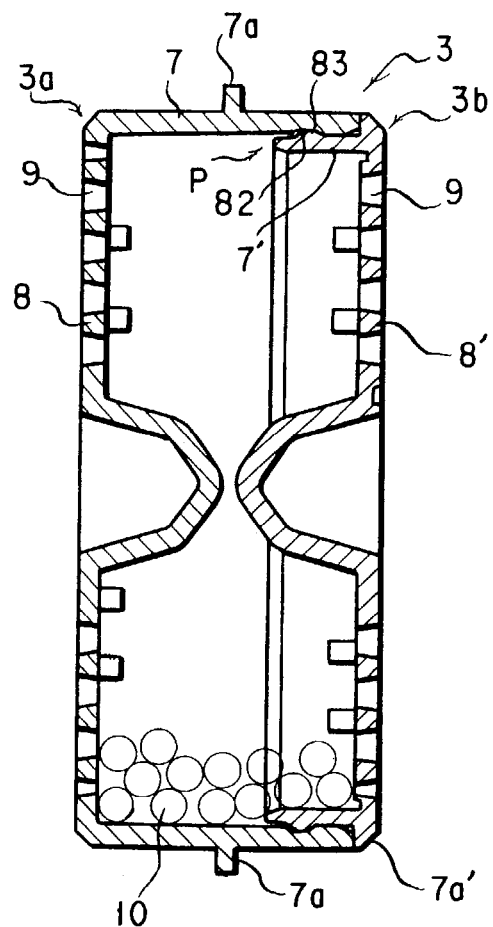
FIG. 13 is a side cross sectional view in elevation illustrating a chemical receptacle for use in the arrangement shown in FIG. 1 to 12.
Figure 14:
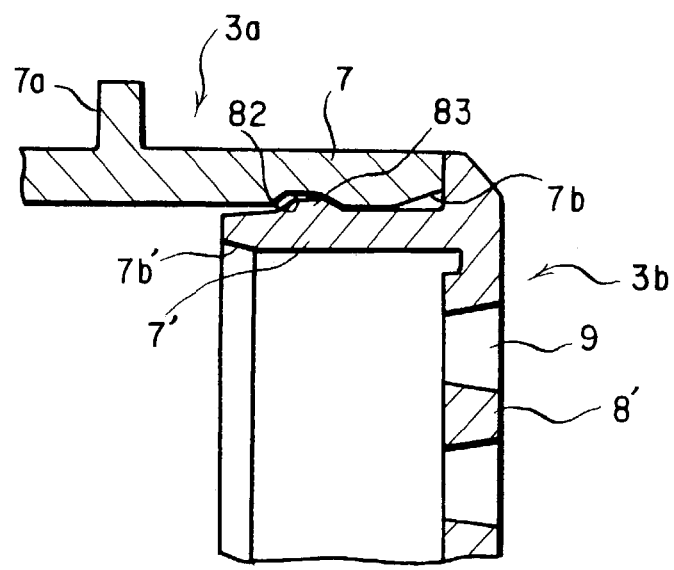
FIG. 14 is an enlarged side cross sectional view illustrating details of the substantial part P shown in FIG. 13.

Further, one of the inner surface of the cylindrical wall 7 of the receptacle main body 3a and the outer surface of the cylindrical wall 7' of the lid body 3b where they are fitted with each other as shown in FIGS. 13 and 14, is formed with an annular recess 82 and the other is formed with an annular projection 83. Furthermore, the receptacle main body 3a is formed on its periphery with an annular projection 7a to enable its detachable engagement with the receptacle retainer 4 in the fan type chemical volatilizing and diffusing apparatus.

The cylindrical wall 7' of the lid body 3b as shown enlarged in FIG. 14 has its inner surface cylindrical surface that is tapered in an end portion 7b' thereof to become wider outwards. On the other hand, the inner surface of the cylindrical wall 7 of the receptacle main body 3a, too, is likewise tapered in an end portion 7b thereof to widen outwards.

With the chemical receptacle 3 so constructed as mentioned above, fitting the cylindrical wall 7' of the lid body 3b into the inner surface of the cylindrical wall 7 of the receptacle main body 3a unites the two bodies 3a and 3b together as shown in FIG. 13. Then, the flange 7a' of the lid body 3b comes into contact with the end face of the cylindrical wall 7 of the receptacle main body 3a. Also, with the annular recess and projection 82 and 83 of the cylindrical walls 7 and 7' brought into engagement with each other, the two bodies 3a and 3b are even more firmly joined together.

This arrangement when the receptacle main body 3a filled with a mass of chemical impregnated discrete bodies or particles 10 is closed with the lid body 3b prevents the chemical impregnated discrete bodies or particles from getting into the end face of the receptacle main body 3a and the end wall of the lid body 3b because it permits the lid body 3b to come to be fitted into the receptacle main body 3a while driving a fraction of chemical impregnated bodies or particles in contact with the cylindrical wall 7 of the receptacle main body 3a to move towards the inside of the receptacle main body 3a.

Then, the outwards widening taper surface 7b' provided at the end portion of the cylindrical wall 7' in its inner surface of the lid body 3b causes the lid body 3b to be fitted into the receptacle main body 3a while thrusting aside the chemical impregnated bodies 10 inwards of the receptacle main body 3a.

The chemical receptacle having the chemical receptacle main body 3a and the lid body 3b fitted with each other is here made symmetrical in shape about the annular projecting engagement rim 7a. This permits the chemical receptacle 3 when inserted into the receptacle retaining section 4 in the fan type chemical volatilizing and diffusing apparatus to be inserted by making either the end wall 8 or 8' face it.

The chemical receptacle 3 is composed of a material that is impermeable with a chemical. For example, aluminum, stainless steel and glass are effective. In an economical consideration, an inexpensive plastic is effective. In this case, a polyester plastic is used that is chemical impermeable, inexpensive and good in both safety and stability. By the way, a technology expected to be significant in future is currently under development, which overcoats an inexpensive resin with a permeation preventing agent without contact.

The chemical receptacle composed of a plastic may be impregnated and/or coated with a UV absorber on its inner and/or outer surface so as to be prevented from degrading by light. The construction material such as plastics may be impregnated with antioxidant to have an enhanced resistance property.

Mention is next made of assembling the apparatus in this form of embodiment as well as its operation.

To build up the apparatus so constructed as mentioned above, the battery case 13 loaded with the battery cells 12 is inserted and loaded into the power supply accommodating section 11 in the cartridge 2, and the chemical receptacle retaining section 4 in the cartridge 2 so loaded is loaded with the chemical receptacle 3 to hold it. The cartridge 2 so loaded is slid along the inner wall 25 into the apparatus main body 1 and thereby incorporated therein. Then, the engagement projections 22 and 22 on the cartridge 2 are engaged with the engagement holes 33 of the apparatus main body 1, the rails 23 and 23 with the grooves 34 and 34, and further the hook 20 on the outer wall 17 of the battery case 13 with the engagement protrusion piece 19; hence the cartridge 2 fitted into engagement with the apparatus main body 1. The engagement protrusion piece 19 is then moved along a cam profile 20a of the hook 20 to engage with a jaw portion of the hook 20.

In this state, the inner airflow opening 24 formed in the upper inner wall 25 of the apparatus main body 1 is opposed to the chemical receptacle 3 in the cartridge 2. Also, the electrical contacts 36 and 36 mounted to one inner, lower side face of the apparatus main body 1 enters the cutouts 16 and 16 from which they come into contact with the terminals of the battery cells 12 and 12 in the battery case 13, thereby making up the electric circuit for the motor 30. Then, the switch 37 is turned ON by sliding the slide piece 39 to drive the motor 30 and in turn the fan 32. Outside air is thus drawn past the chemical receptacle 3 to flow in through the inner airflow opening 24, which past the duct 29 is discharged through the outer airflow opening 28. This causes the chemical ingredient impregnated in the chemical impregnated body 10 within the chemical receptacle 3 to volatilize in the airflow passing therethrough and then to diffuse through the outer airflow opening 28 into the atmosphere. The airflow that the fan 32 produces in the apparatus in this way does flow remote from the battery 12.

Turning the switch 37 ON for the driving of the fan 32 also electrically energizes the pilot lamp 38 to light it, indicating that the apparatus is in operation. Further, the timer 38a if included in the switch circuit enables the state of the apparatus turned ON to be switched OFF after a given time period.

The cartridge 2 is detached from the apparatus main body 1 by pressing the loading release button 6 inwards to disengage the engagement protrusion piece 19 from the hook 20.

The outer airflow opening 28 is formed with a plurality of cross pieces 28a to allow air to flow out past interstices between formed thereby. These cross pieces 28a are provided to prevent entry of a finger or a foreign matter into the apparatus main body 1, and to play a role to avert a danger and to prevent the fan from halting.

For the pilot lamp 38 that is lit by its electrical energization with the switch 37 turned ON, use is advantageously made of a light emitting diode (LED) to save consumption of the battery energy. An LED consumes only 15% or less of the total current consumption of the apparatus. The pilot lump 38 then gradually falls off in intensity as the battery falls in voltage, and goes out when it becomes dead.

Also in the form of construction described, the chemical receptacle 3 used can be altered in volume or size as desired simply by changing the size of projection of its retainer 2b from the chemical receptacle retaining section 4.

On the other hand, the battery cells 12 used can be altered in number and size, D(R20), C(R14), AA(R6), as desired by changing the size of the power supply accommodating section 11 of the power supply housing 2a and the size of the battery case 13.

Figure 17:
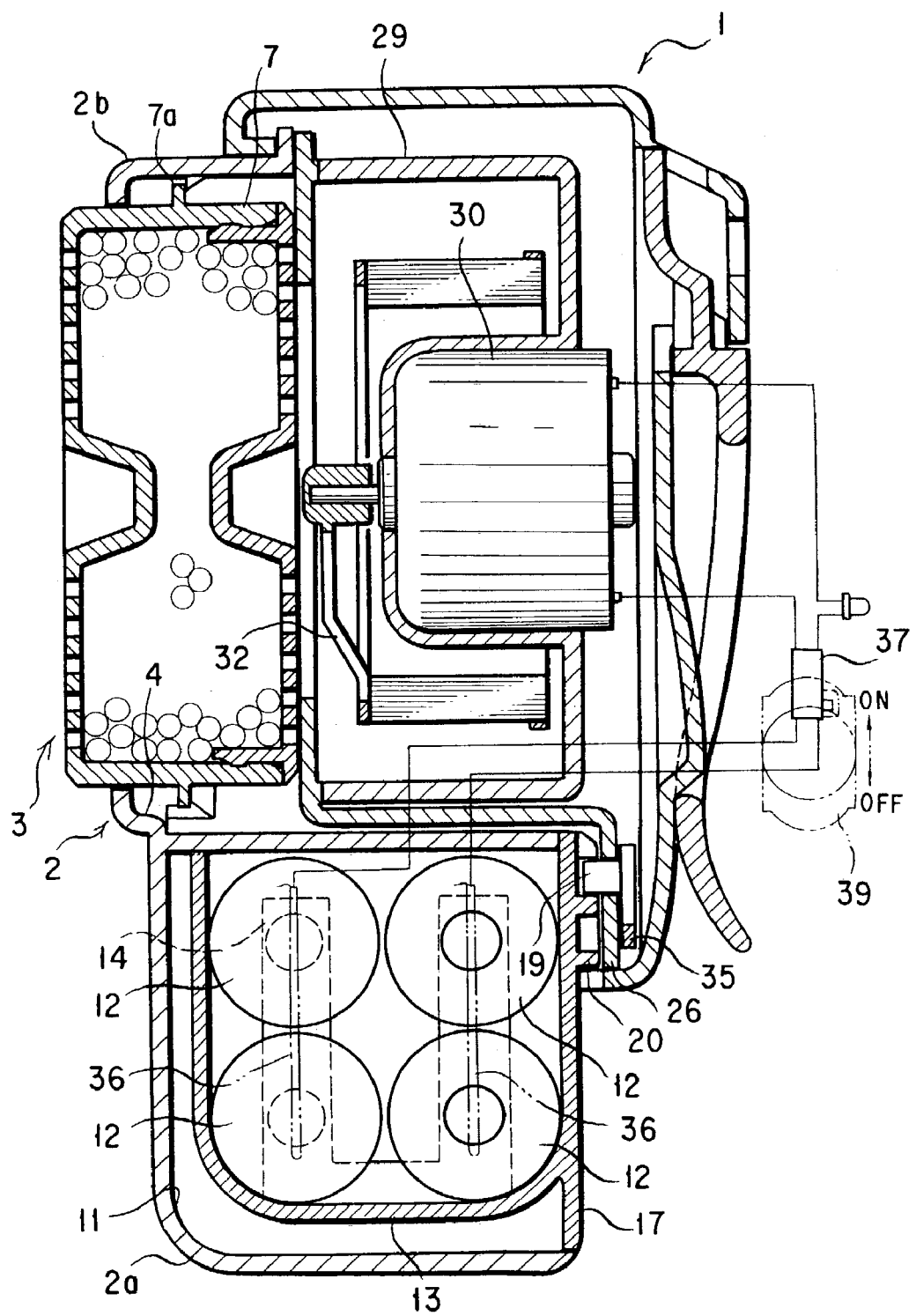
FIG. 17 is a side cross sectional view in elevation illustrating a fan type chemical diffusing apparatus that represents a second form of embodiment of the present invention in which four (4) battery cells are accommodated in the power supply housing.

FIG. 17 shows an example as the second form of the apparatus according to the present invention in which the power supply accommodating section 11 and the battery case 13 in the power supply housing 2a are made larger in size to have four battery cells 12 accommodated therein. In this instance, leaving the hook 20 unaltered in position on the outer wall 17 of the battery case 13 allows the apparatus main body 1 to be used in common as it is without changing its size. Further, changing the apparatus main body in volume with respect to the cartridge 2 can change the fan and the motor in volume as desired.

In these forms of embodiment of the invention, variations in size of the chemical receptacle 3 may be prepared that vary in chemical consumed (lasting) time period for selection and interchange. Further, variations in battery capacity of the power supply housing 2a may be prepared that vary in battery exhausted (used up) time period for selection and interchange. Furthermore, the ability in the forms of embodiment described to change the apparatus main body 1 in volume makes it possible to change the fan and motor (blower) in size to be included therein, thereby permitting a desired wind velocity and airflow capacity to be selected in compliance with a place where the apparatus is used. And, the apparatus according to the present invention has enabled the time period for the chemical to be used up and the time period for the battery to be used up to coincide with each other. This makes it possible for the apparatus when the chemical therein has lost its efficacy to become ready for reuse just upon exchanging the cartridge 2.

While in describing the foregoing forms of embodiment, mention is made of using a battery for the power supply, the power supply may be a commercial power supply. Then, the power supply accommodating section 11 in the power supply housing 2a is provided with a plug to be inserted to a domestic plug socket and has a power converter incorporated therein that converts commercial electric power to power in the form adapted for the motor 30 to drive the fan 32. It is also possible to make the apparatus usable with either the commercial power supply or the battery on selection. For example, in the use of the commercial power supply, the circuit for the battery is made blocked from the circuit for the apparatus main body.

Alternatively, the power supply may be a rechargeable battery that is charged as it may or does demand.

As will be apparent from foregoing description, it has become possible to relatively position the chemical receptacle 3 and the power supply so each of them receives substantially no limitation in capacity or volume from the other. It has also become possible to position the chemical receptacle 3 relative to the chemical receptacle retainer 2a so it receives substantially no limitation in volume (no limitation in its axial size) from the latter. On the other hand, the apparatus main body 1 receives substantially no limitation in volume relative to the cartridge 2, either.

While in the forms of embodiment so far described, the chemical receptacle 3 is shown inserted from the inside of the chemical receptacle retaining section 4 of the chemical receptacle retainer 2b and brought into engagement and retained therewith upon the annular projecting engagement rim 7a getting over across the one set of projecting piece 21b as shown in FIGS. 4 and 17 etc., it may be made possible to insert the chemical receptacle 3 into the chemical receptacle retaining section 4 of the chemical receptacle retainer 2a from the outside thereof.

Figure 18:
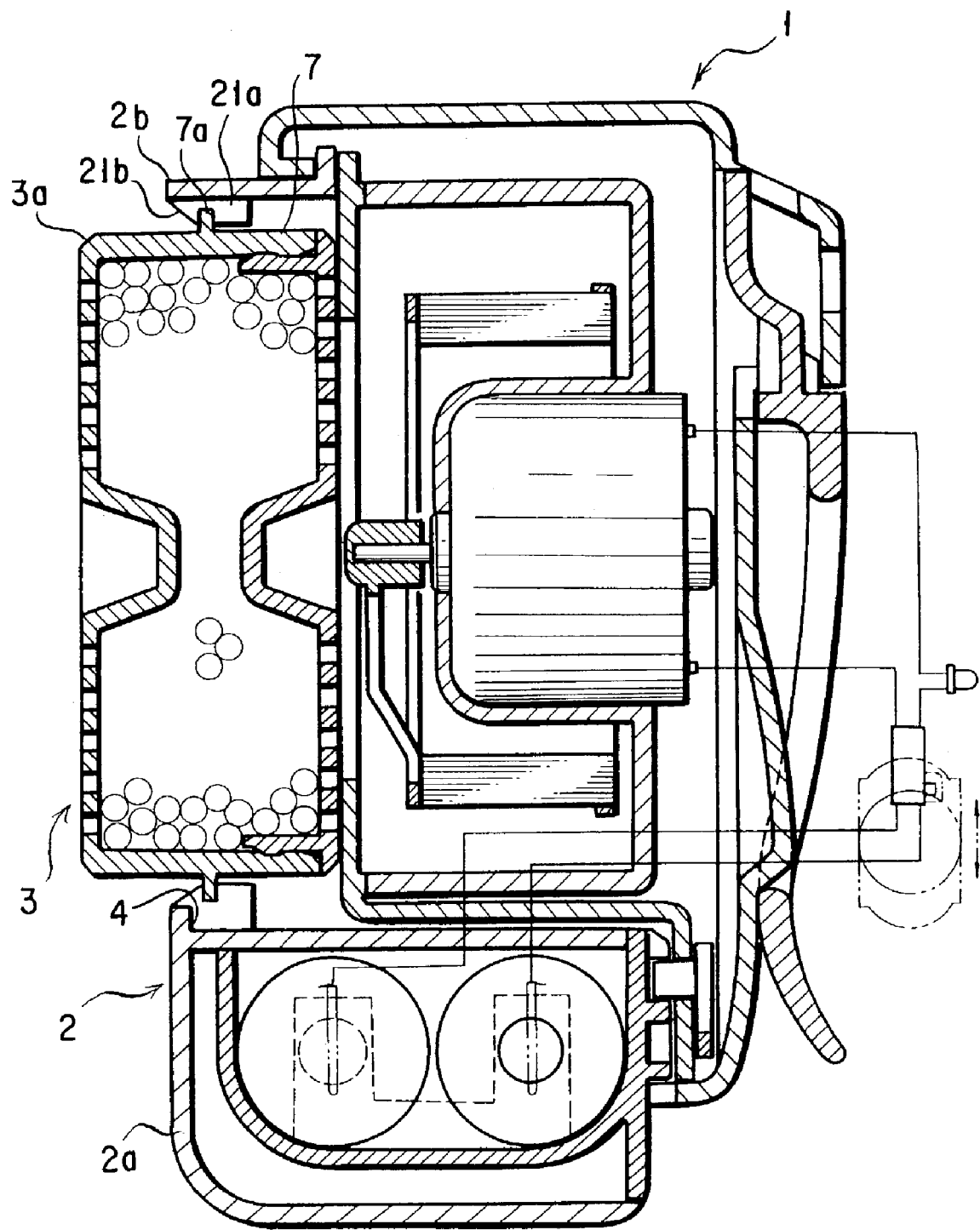
FIG. 18 is a similar view illustrating a fan type chemical diffusing apparatus that represents a third form of embodiment of the present invention in which the chemical receptacle is loaded into a chemical receptacle retainer in the cartridge from its outer side.

FIG. 18 shows such an example as the third form of embodiment of the invention in which the receptacle retaining section 4 of the receptacle retainer 2a has its outer open end sufficient in size to accept the annular projecting engagement rim 7a formed on the chemical receptacle 3. A first and a second set of more than one, e.g., three projecting pieces 21a and 21b are here again formed both rising from the inner surface of the receptacle retaining section 4 and designed to axially catch and hold the annular projecting engagement rim 7a between them. Here, the set of projecting pieces 21b are arranged to lie at the outer open end of the receptacle retaining section 4 and outer of the projecting pieces 21a, permitting the chemical receptacle 3 to be inserted from the outside of the chemical retainer 2b and caught held by the receptacle retaining section 4 upon the annular projection 7a getting over across the projecting pieces 21b. It is also made possible to insert the chemical receptacle 3 into the chemical receptacle retaining section 4 of the chemical retainer 2b from the outside thereof by providing an arrangement in which the chemical receptacle 3 is threaded into the chemical receptacle retaining section 4.

Adopting this form of embodiment make it possible to exchange the chemical receptacle 3 without disengaging the cartridge 2 from the apparatus main body 1 and thus facilitates exchanging the chemical receptacle 3.

Figure 19:
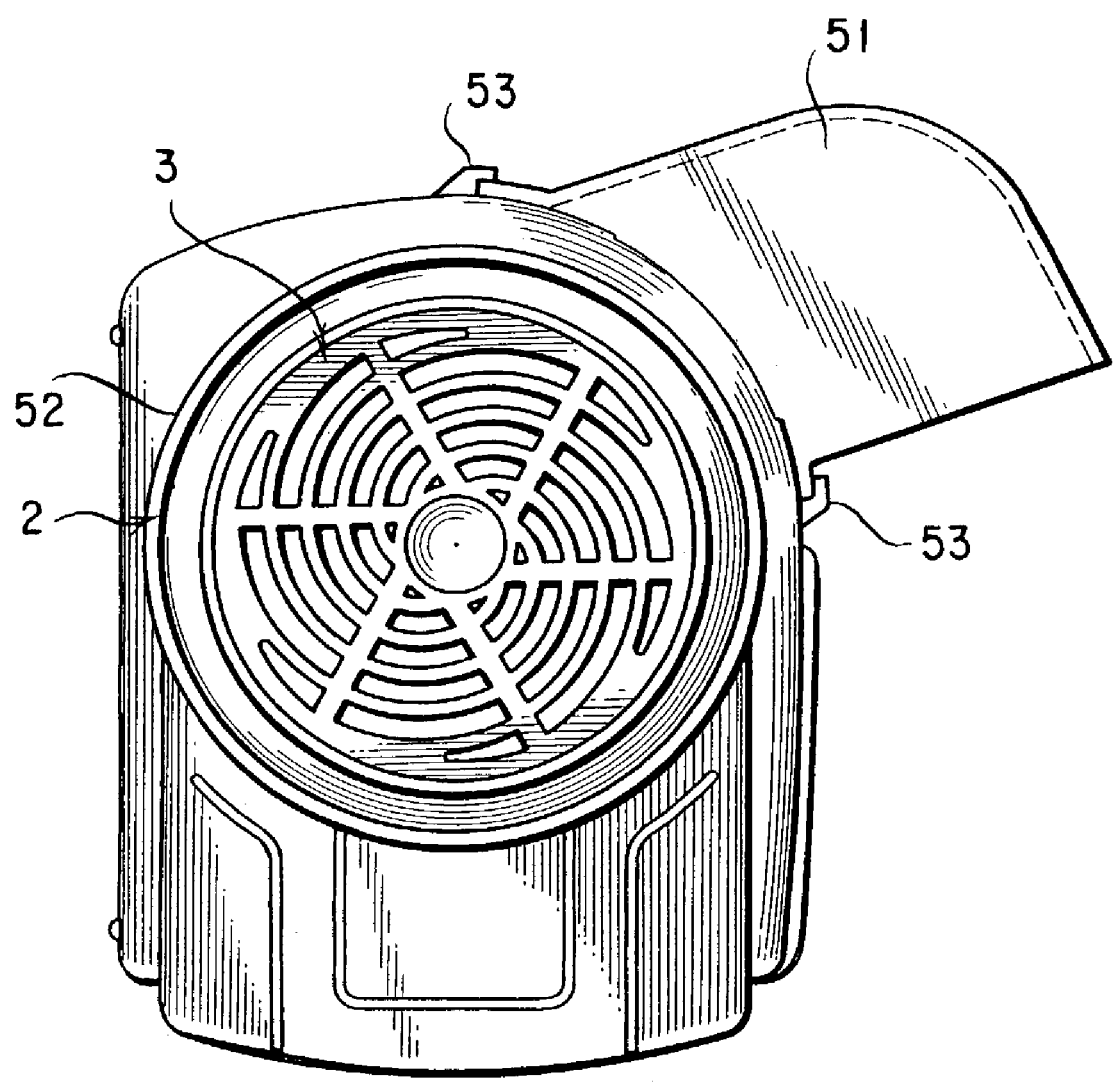
FIG. 19 is a front elevational view illustrating a fan type chemical diffusing apparatus that represents a fourth form of embodiment of the present invention in which hoods are attached to airflow orifices and a chemical receptacle retainer of the cartridge at their outer sides, respectively.
Figure 20:
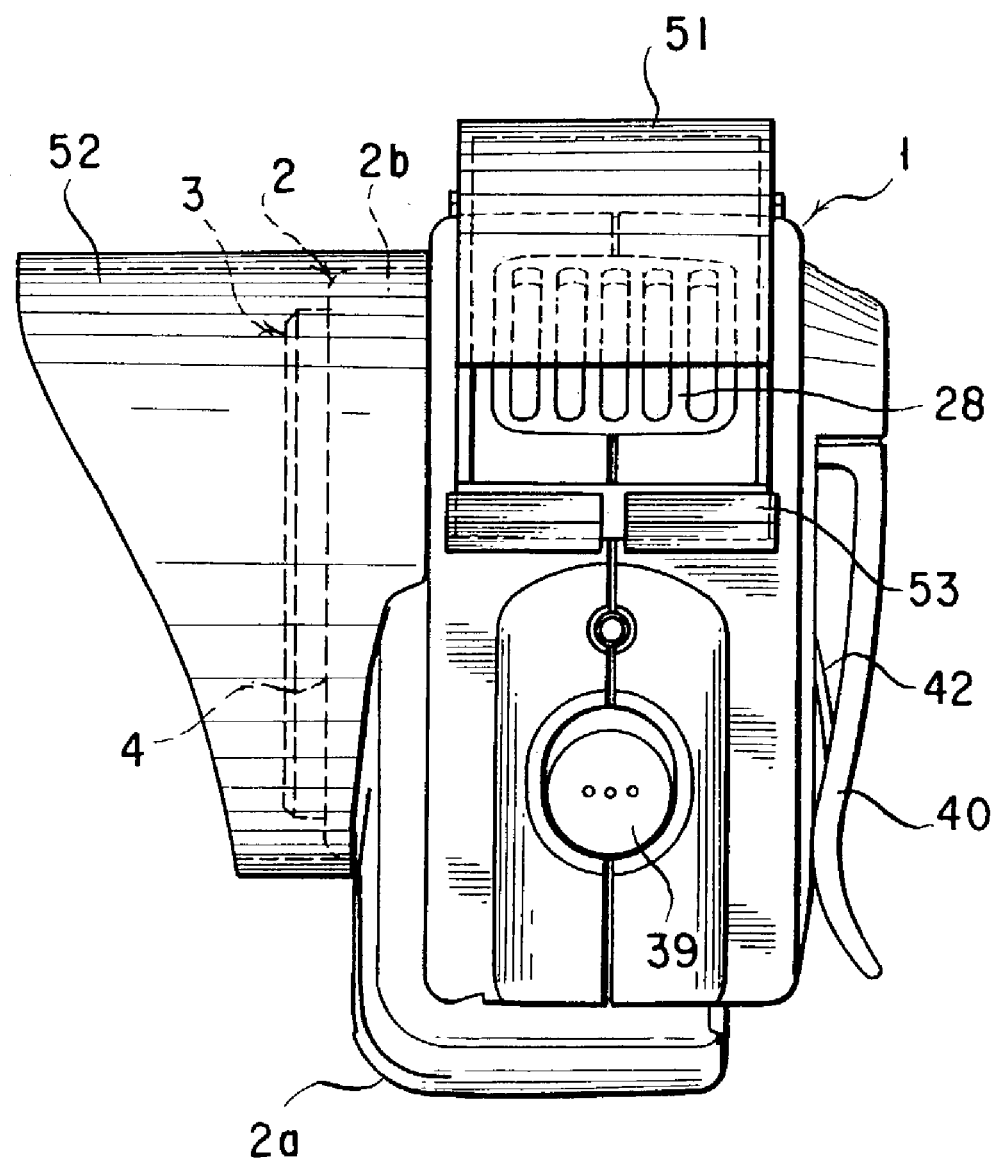
FIG. 20 is a side elevational view of the apparatus shown in FIG. 19.

FIGS. 19 and 20 show the fourth form of embodiment of the present invention in which the outside of the outer airflow opening 28 and the outside of the chemical receptacle retaining section 4 in the apparatus main body are covered with a first and a second hood 51 and 52, respectively.

The first hood 51 is configured so as to cover the upper side of the outer airflow opening 28 therewith and designed to lie detachably held by engagement portions 53 mounted on an area in the periphery of the outer airflow opening 28.

On the other hand, the second hood 52 is made in the form of a cylinder with its upper side made longer like a pent roof and is designed to stay disengageably fitted over the outward projection of the chemical receptacle retaining section 4 of the chemical receptacle retainer 2a.

This form of embodiment of the apparatus prevents in a rainfall drops of rain from getting into the outer airflow opening 28 and wetting the chemical in the chemical receptacle 3.

Figure 21:
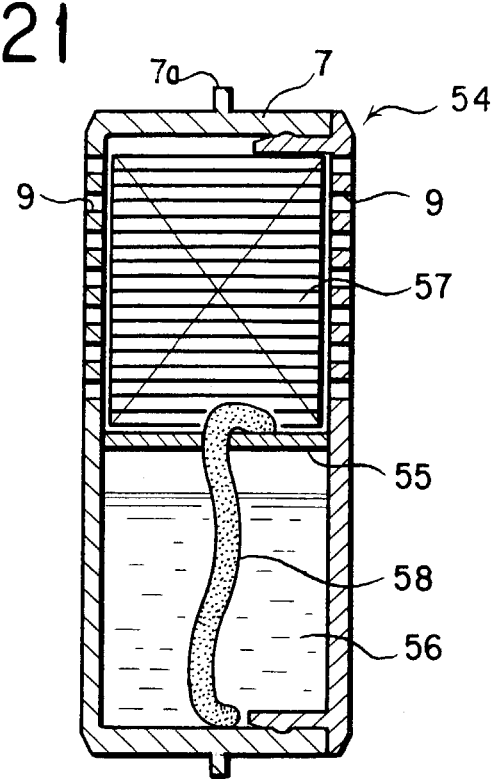
FIG. 21 is a side and cross sectional view in elevation of a chemical receptacle, illustrating a fan type chemical diffusing apparatus that represents a fifth form of embodiment of the present invention in which use is made of a liquid chemical.
Figure 22:
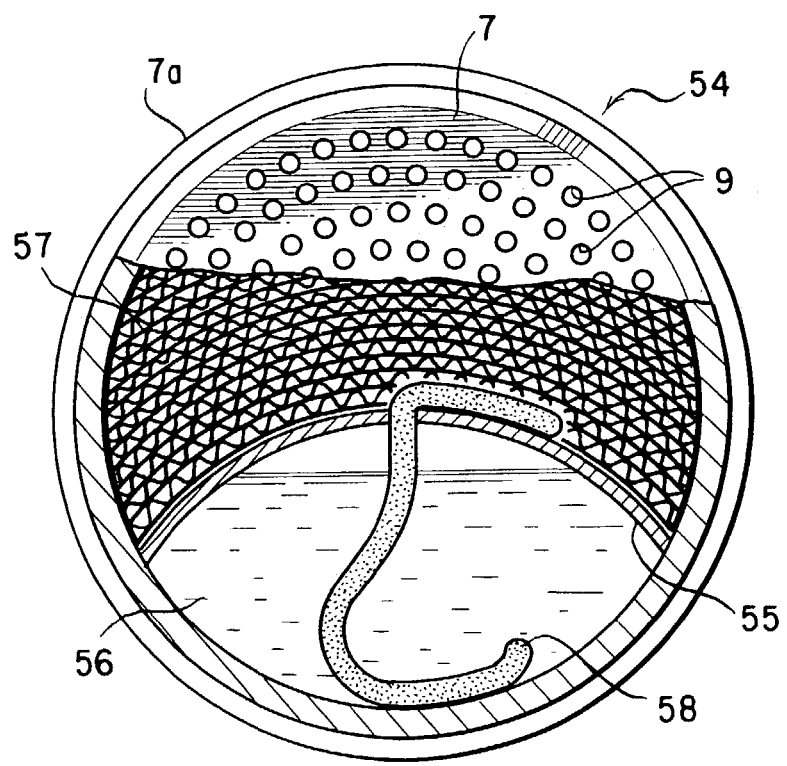
FIG. 22 is a front elevational view in part broken of the chemical receptacle shown in FIG. 21.

While in the forms of embodiment so far described, a chemical receptacle 3 is shown which is filled with a chemical impregnated body 10 that is impregnated with a chemical therein, it is possible to use, as shown in FIGS. 21 and 22, a chemical receptacle 54 that is divided by a partition plate 55 into two compartments one of which is filled with a liquid chemical 56 and the other of which is loaded with an impregnatable body 57. The body 57 is here impregnated with the liquid chemical 56 by means of a siphoning cord 58 passing through the partition 55. In this case, the liquid chemical impregnated in the body 57 is allowed to volatilize in an airflow passing though the chemical receptacle 54 and thereby emitted into the outside.

In this form of embodiment, the chemical receptacle 54 having its own upper and lower sides as mentioned above needs to be fitted with the chemical receptacle retaining section 4 of the cartridge 2 so that the compartment in which the liquid chemical 56 is stored lies in the underside while the apparatus is in service.

Figure 23:
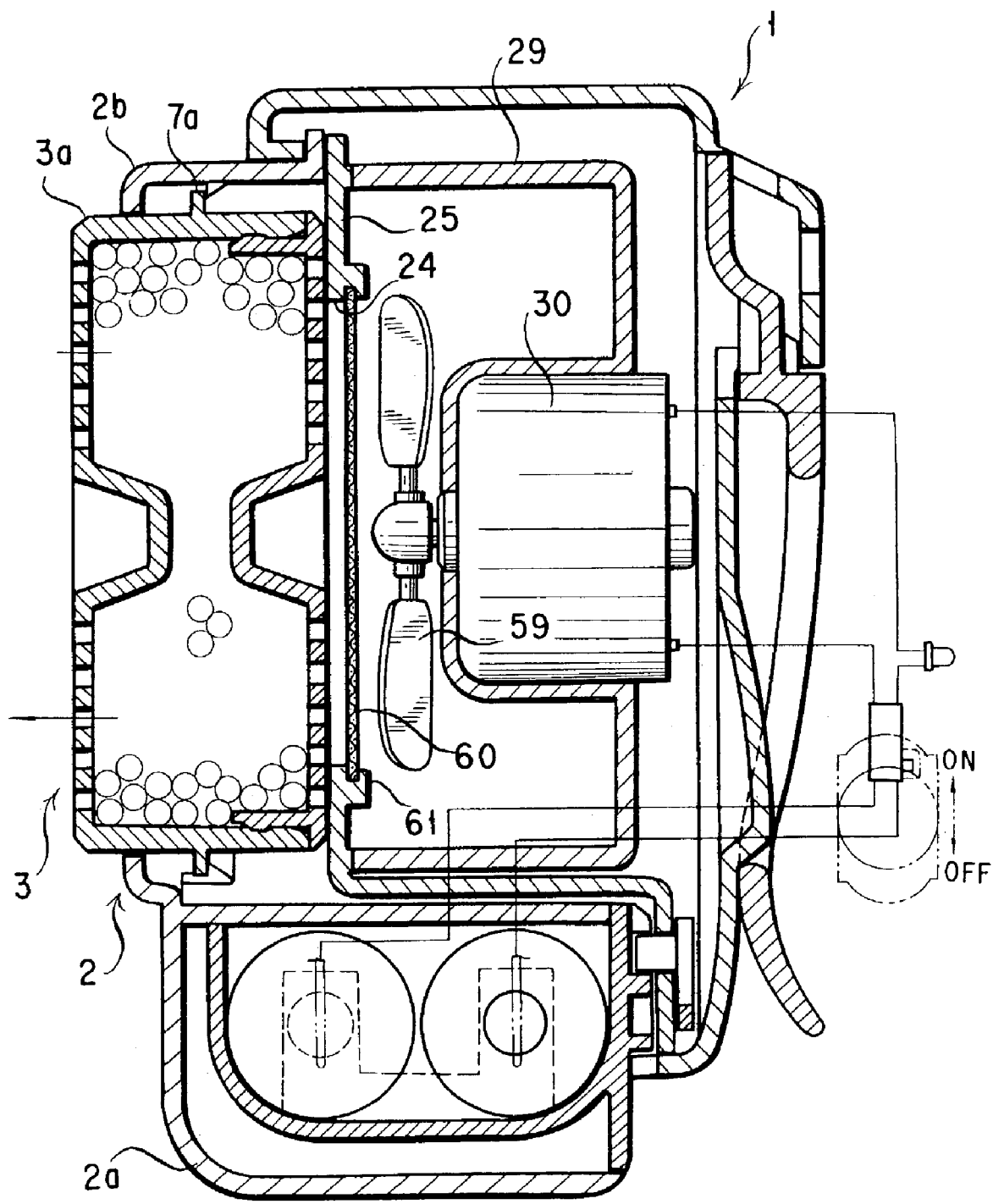
FIG. 23 is a side cross sectional view in elevation illustrating a fan type chemical diffusing apparatus that represents a sixth form of embodiment of the present invention in which use is made of an axial fan and a heater.

FIG. 23 shows the sixth form of embodiment of the present invention that reverses the direction of the airflow with respect to the chemical receptacle 3 and permits the airflow to be heated while passing through the chemical receptacle 3.

Specifically in this form of embodiment, an axial fan 59 is coupled to the drive shaft 31 of the motor 30 so that the fan 59 faces the inner airflow opening 24 and, when the motor 30 is driven, produces an airflow directed to pass through the inner airflow opening 24 towards its outside. Further, a heater 60 in the form of a disk is mounted between the fan 59 and an end face of the inner airflow opening 24 as held in an annular recess 61 formed in the upper inner wall 25. The heater 60 is electrically connected in an electric circuit (not shown) to the power supply, parallel to the motor 30 driving the fan 59. An ON/OFF switch included in the electric circuit permits the heater 60 to be energized to heat up when needed.

In this form of embodiment, a chemical volatilizing and diffusing air is emanated outwards of the chemical receptacle 3. Heating up the heater 60 makes it possible to raise the temperature of the airflow passing through the chemical receptacle 3 to accelerate chemical volatilization from the chemical integrated body 10 held in the chemical receptacle 3. And, in this case, air is taken in through the outer airflow opening 28.

Figure 24:
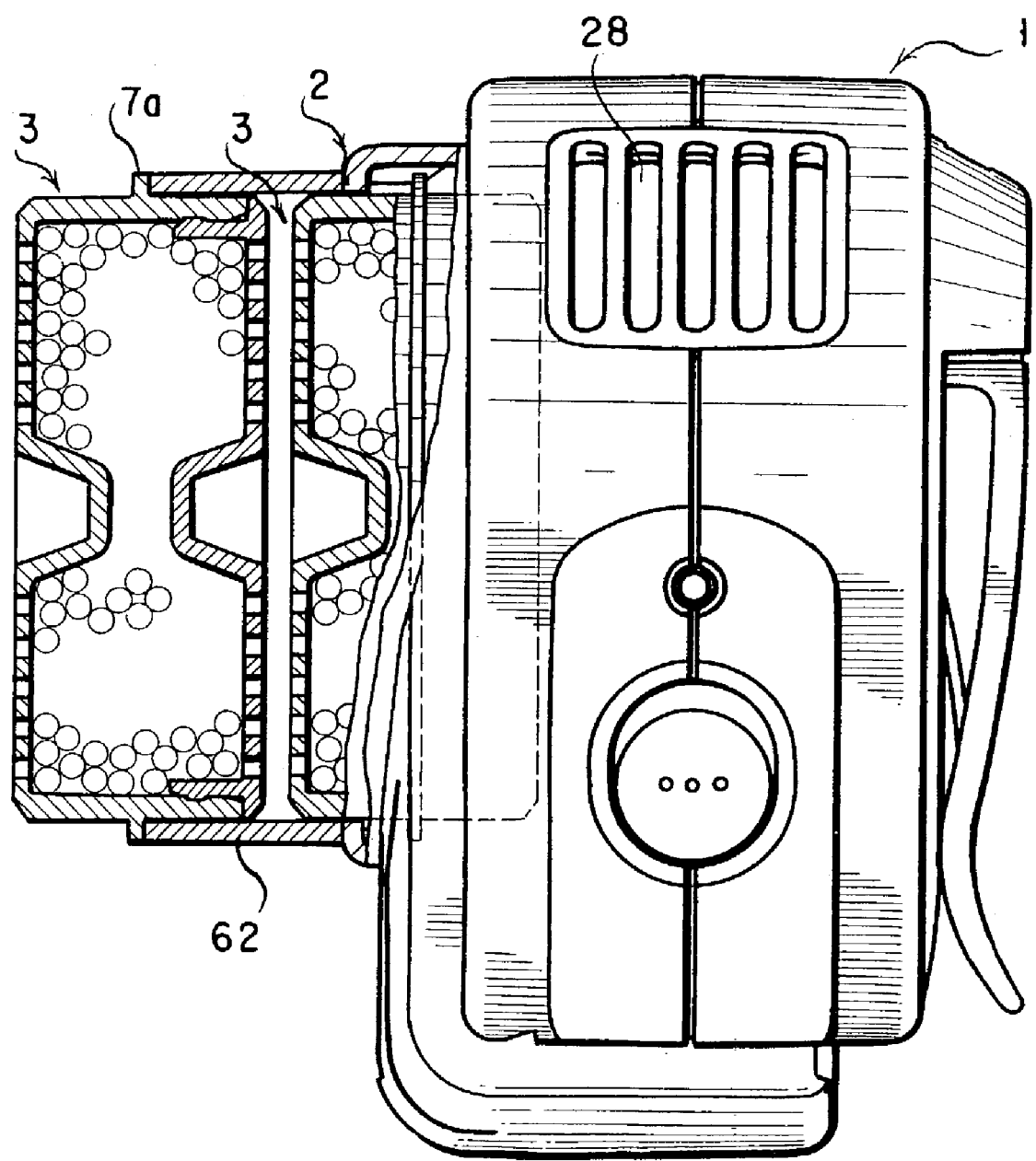
FIG. 24 is a side elevational view in part broken and cross sectional illustrating a fan type chemical diffusing apparatus that represents a seventh form of embodiment of the present invention in which two chemical receptacles are coupled together using a coupling cylinder.
Figure 25:
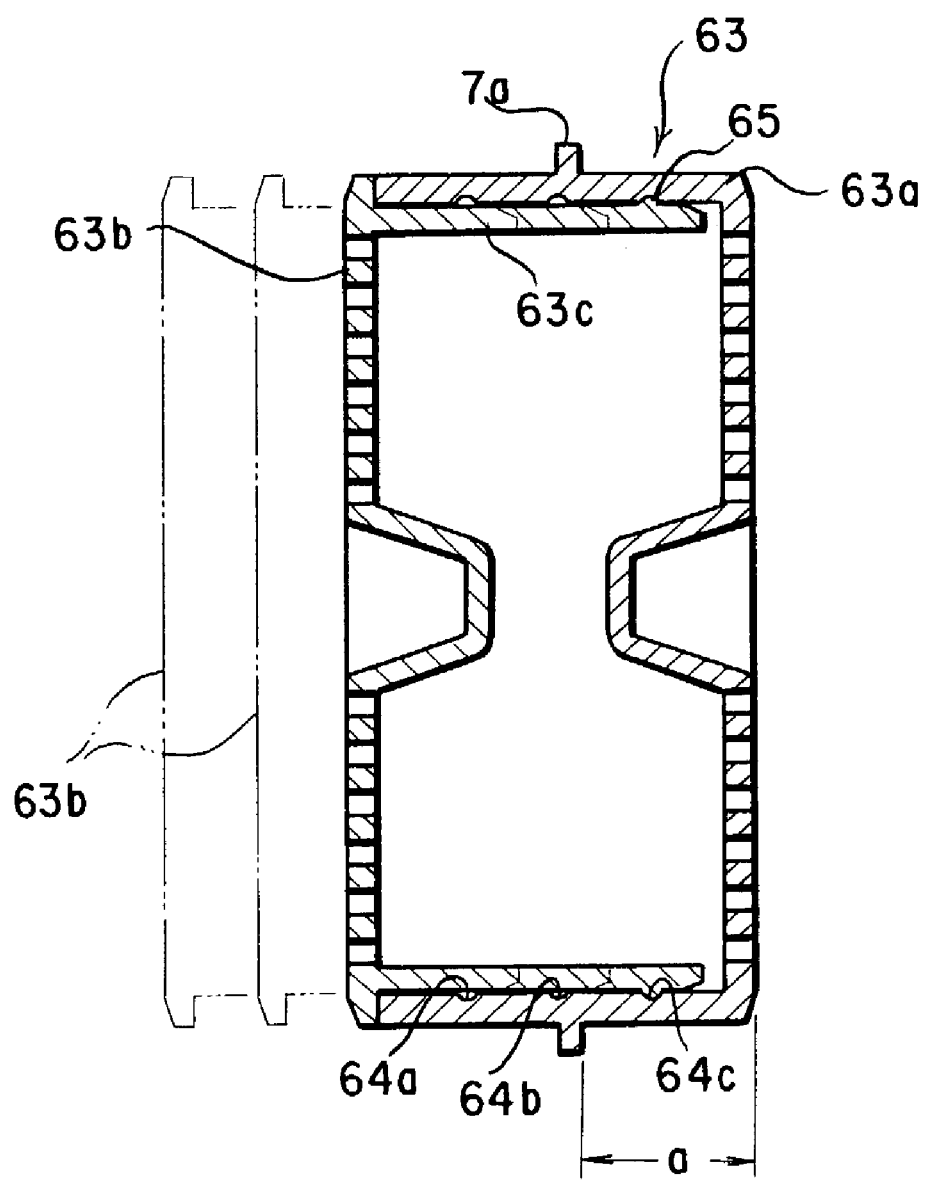
FIG. 25 is a side cross sectional view in elevation of a chemical receptacle, illustrating a fan type chemical diffusing apparatus that represents an eighth form of embodiment of the present invention in which use is made of a chemical receptacle that is variable in volume.

Forms of embodiment shown in FIGS. 24 and 25 represent examples in which the chemical receptacle 3 attached to the apparatus for service is made variable in chemical capacity.

That is, FIG. 24 show the seventh form of embodiment of the present invention in which in the cartridge 2 holding the chemical receptacle 3 in the chemical receptacle retainer 2b, one end of a coupling cylinder 62 is fitted over a portion of the chemical receptacle 3 that is exposed from the chemical receptacle retainer 2b and another chemical receptacle 3 is fitted into the other end of the coupling cylinder 62.

This form of embodiment enables two chemical receptacles 3 to be coupled together coaxially by means of the coupling cylinder 62, and makes the chemical capacity in service twice as large as in the previous forms of embodiment.

Also in this form of embodiment, the use of a plurality of coupling cylinders 62 permits a plurality of chemical receptacles 3 to be coupled one to another in succession and allows the chemical capacity in service to be selected at any desired multiple of that for a single chemical receptacle. Further, the coupling cylinder 62 may be configured to extend its cylindrical wall from the annular projecting engagement rim 7a on the chemical receptacle 3 so that it may be united with this additional receptacle 3. Still further, the fit may be not only a slide fit but also a thread fit.

FIG. 25 shows an example as the eighth form of embodiment of the present invention in which a single chemical receptacle 63 can have its chemical capacity varied according to the position at which its lid body 63b is fitted into its main body 63a.

The receptacle main body 63a here is formed in its inner surface with three annular grooves 64a, 64b and 64c axially spaced apart by a suitable distance. On the other hand, the lid body 63b has an elongated cylindrical sidewall (engagement portion) 63c that can be fitted into the receptacle main body 63a and on which an annular projection 65 is formed for engagement with any one of these annular grooves 64a, 64b and 64c. And, selecting which of these annular recesses 64a, 64b and 64c in the receptacle main body 63a the annular projection 65 on the cylindrical sidewall 63c is engaged with variably establishes the depth of fit by which the cylindrical sidewall 63c can be fitted with the receptacle main body 63a and hence the capacity of the chemical receptacle 63.

The annular projecting engagement rim 7a on the receptacle main body 63a in the chemical receptacle 63 according to this form of embodiment is positioned spaced apart from the bottom surface by the same distance a as in the chemical receptacle 3 shown in FIG. 4. This makes it possible for this chemical receptacle 63 to be detachably engaged with the chemical receptacle retainer 2b of the cartridge 2 and held thereby in the same manner as the chemical receptacle 3 shown in and described in connection with FIG. 4.

In this form of embodiment, the capacity or volume of the chemical receptacle 63 is varied stepwise by an amount corresponding to the distance or spacing between adjacent annular recesses 64a to 64c.

Instead of the slid fit described, adopting a threaded coupling by threading the cylindrical sidewall of the lid body into the receptacle main body to form the chemical receptacle makes it possible to steplessly change the depth or extent to which the lid body is inserted and in turn the volume of the receptacle, by changing the depth of threading.

Figure 26:
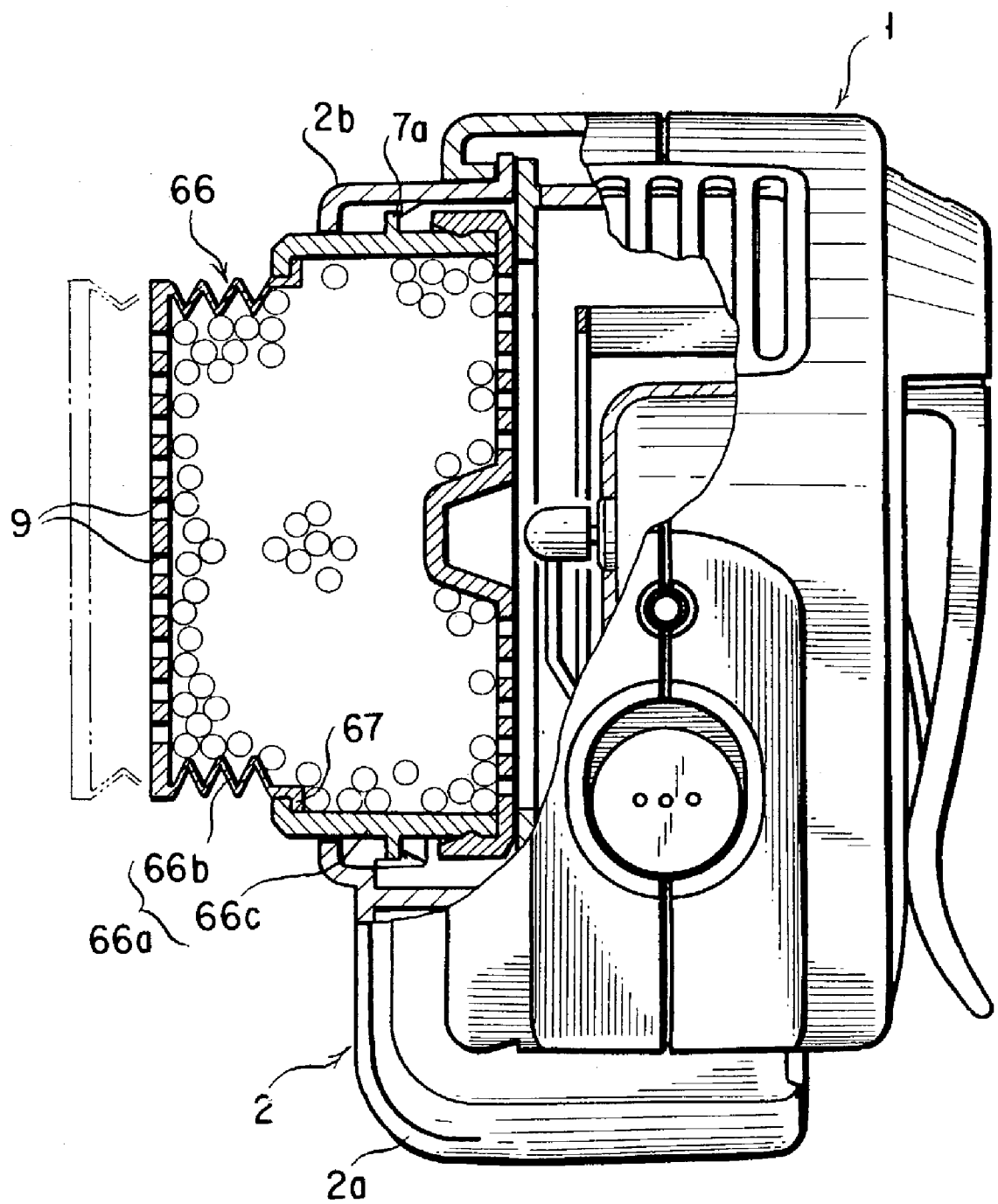
FIG. 26 a side elevational view in part broken and cross sectional illustrating a fan type chemical diffusing apparatus that represents a ninth form of embodiment of the present invention in which use is made of a chemical receptacle that is the form of bellows.

FIG. 26 shows the ninth form of embodiment of the present invention as an example that employs a bellows for the sidewall of a chemical receptacle 66 in its receptacle main body 66a. The receptacle main body 66a of the chemical receptacle 66 is made of an inner portion 66c located inside of the chemical receptacle retainer 2b and an outer portion 66b exposed from the latter, and which portion 66b is here constituted with the bellows. The outer portion 66b has its one end face formed with a large number of vent holes 9 and has at its other end a flange 67 that comes into engagement with an end of the inner portion 66c.

In this form of embodiment, changing the degree of expansion and contraction of the bellows forming the outer portion 66b enables the chemical capacity in the chemical receptacle 66 to be varied.

Figure 27:
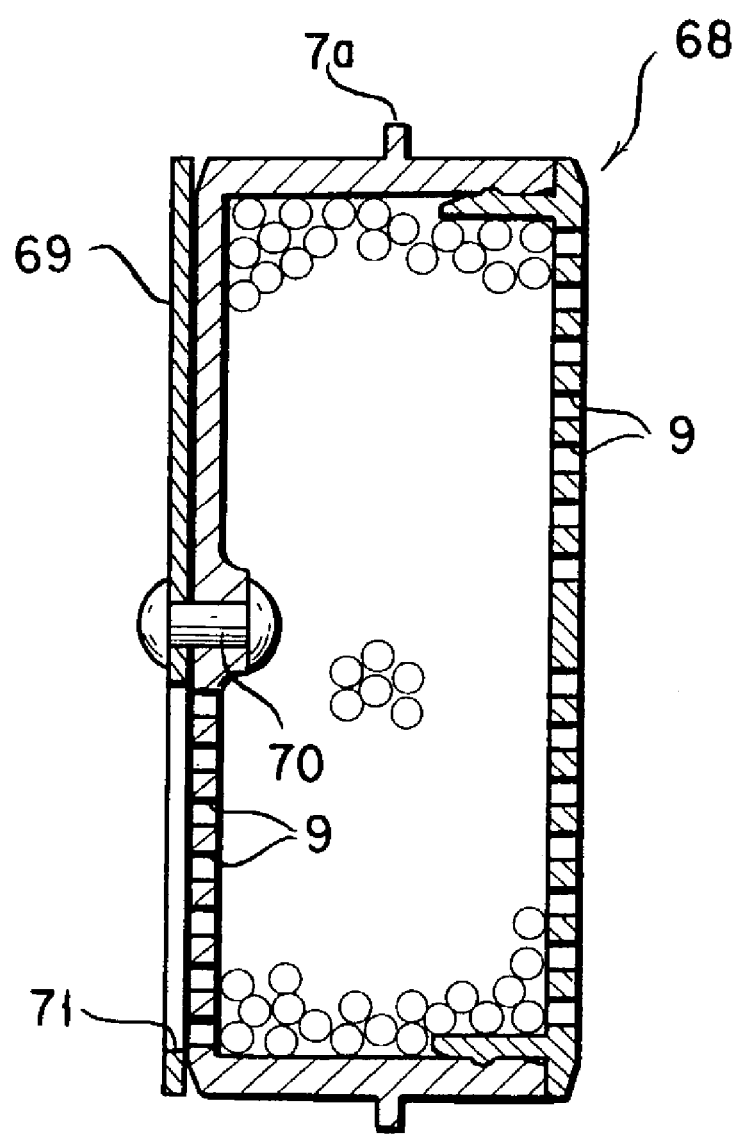
FIG. 27 is a side cross sectional view in elevation of a chemical receptacle, illustrating a fan type chemical diffusing apparatus that represents a tenth form of embodiment of the present invention in which the rate of flow of air passing through its interior is made controllable.
Figure 28:
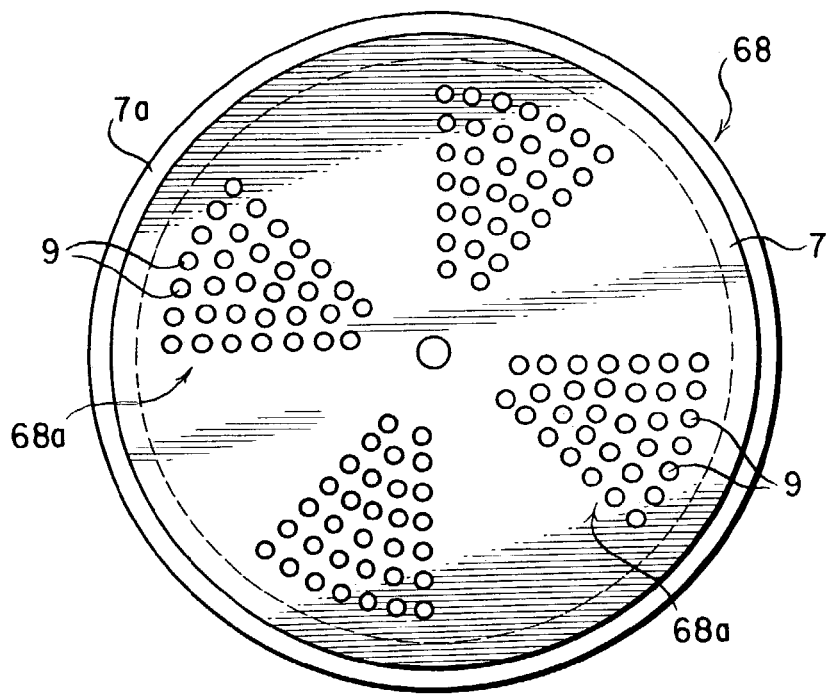
FIG. 28 is a front view illustrating one side end surface of the chemical receptacle shown in FIG. 27.
Figure 29:
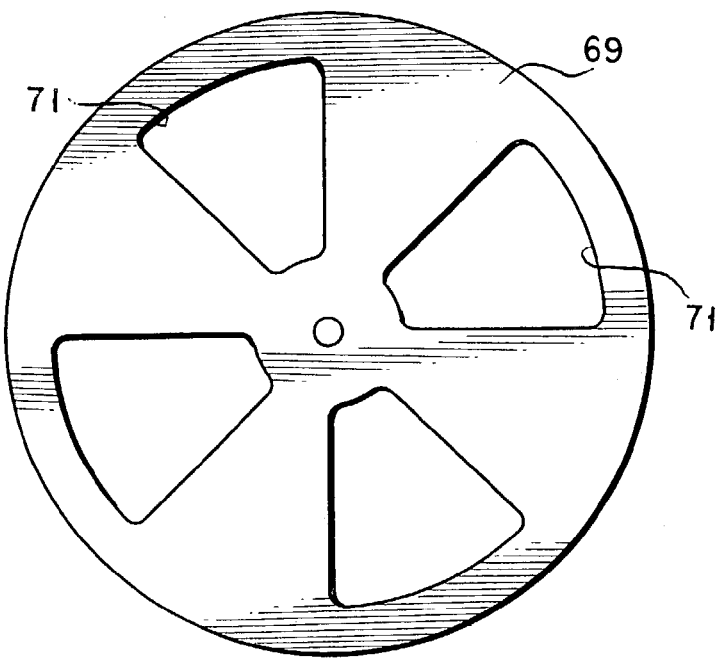
FIG. 29 is a front view illustrating a shutter provided for the chemical receptacle shown in FIGS. 27 and 28.

FIGS. 27 to 29 shows the tenth form of embodiment of the present invention as an example in which changing the airflow rate passing through a chemical receptacle 68 varies the rate of volatilization of the chemical therefrom.

The chemical receptacle 68 has a pair of end faces each of which is formed with vent holes 9. One of these end faces is provided with a plurality of radially extending vent regions 68a equiangularly spaced apart from one another about its center and in which such vent holes 9 are formed as shown. And, the one end face in its outside has a shutter 69 mounted turnably supported on a pin 70, and the shutter 69 is formed with a plurality of radially extending open windows 71 equiangularly spaced apart from one another. This shutter 69 when turned is designed to uncover with these open windows 71, and to cover with its unopen areas, the vent holes 9 in the vent regions 68.

Thus in this form of embodiment, changing the areas that the open windows 71 overlap with the vent regions 68a for the chemical receptacle 68 enables the rate of the airflow through the chemical receptacle 68 to be adjusted.

Figure 30:
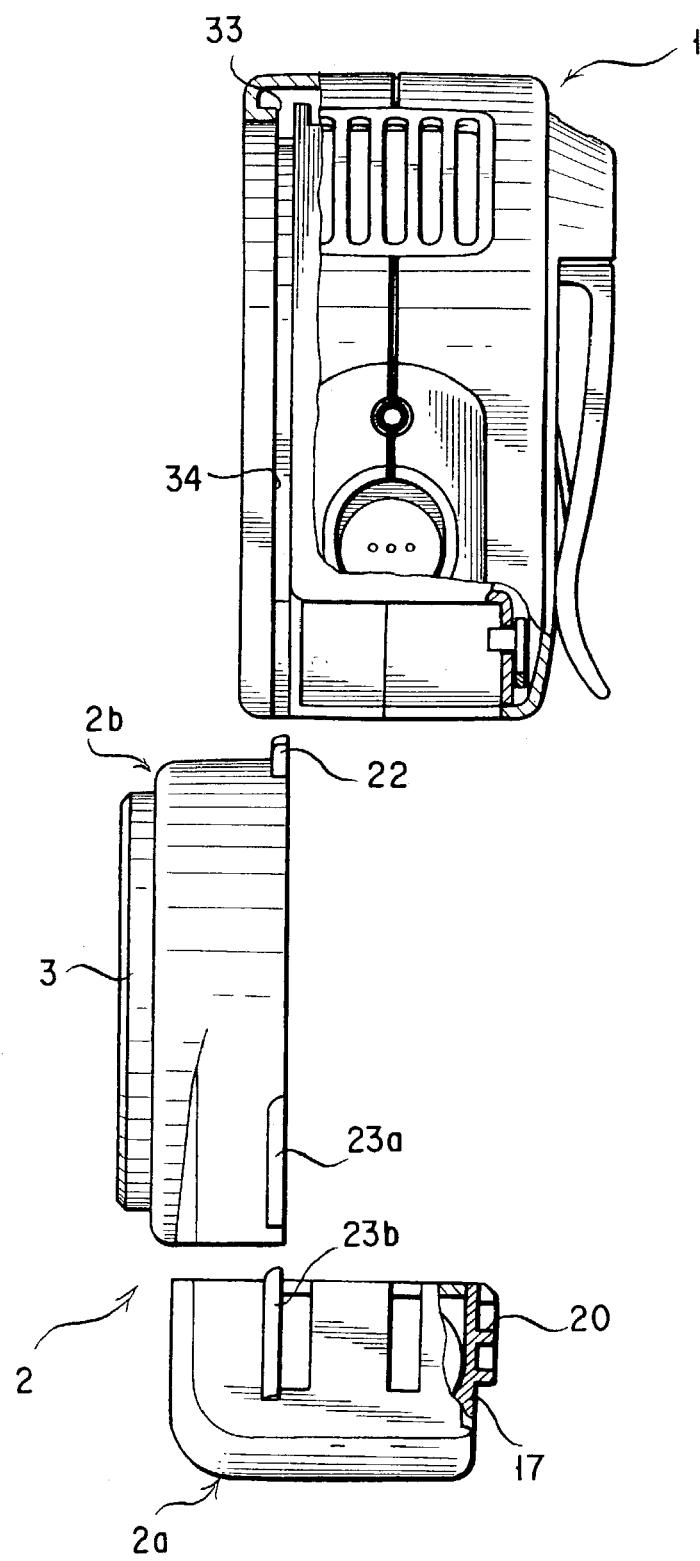
FIG. 30 is a side view decomposed in elevation illustrating a fan type chemical diffusing apparatus that represents an eleventh form of embodiment of the present invention in which the cartridge made detachable from the apparatus main body is made separable into the power supply housing body and the chemical receptacle retaining body.
Figure 31:
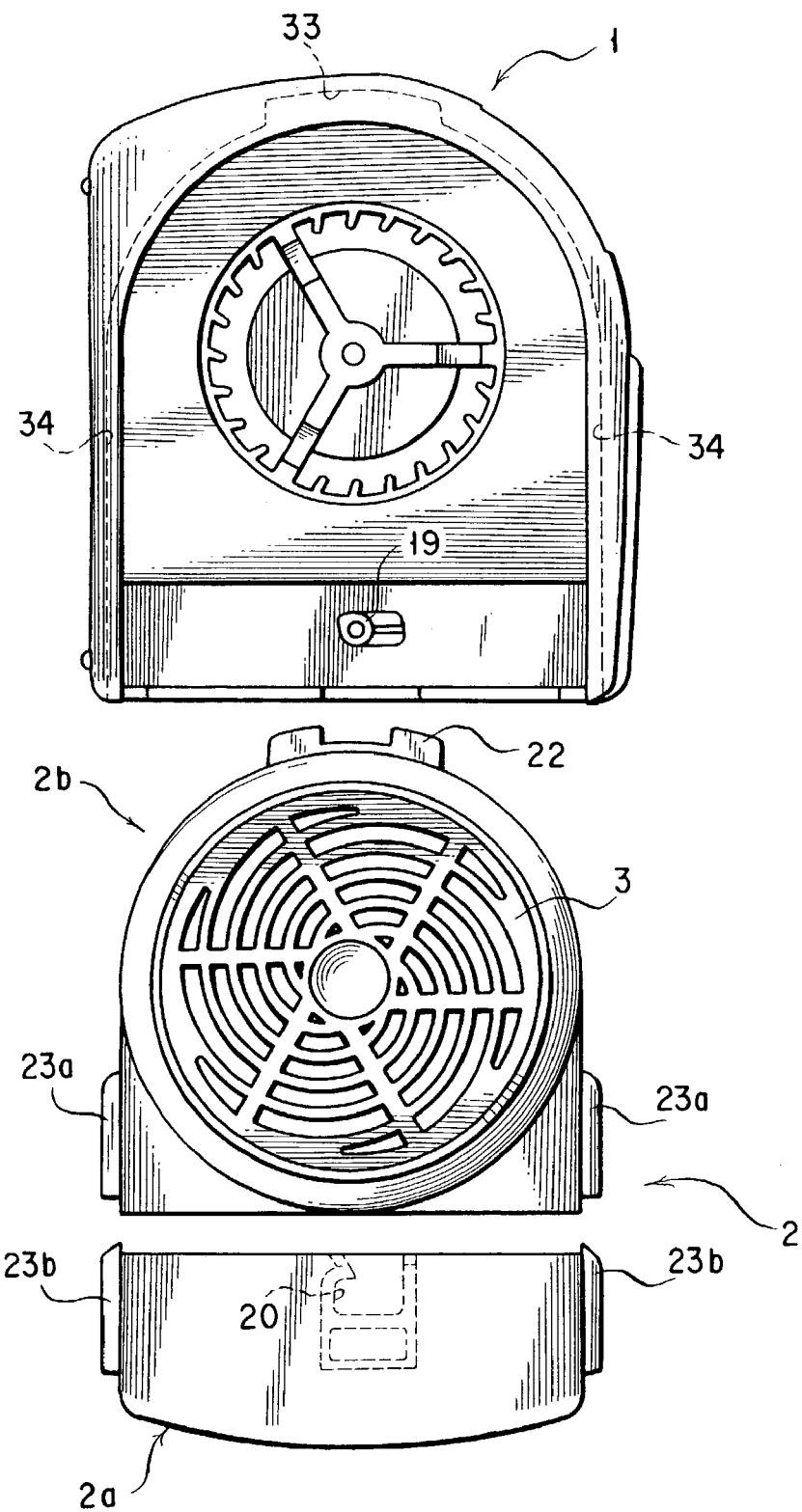
FIG. 31 is a front view decomposed in elevation of the apparatus shown in FIG. 30.

FIGS. 30 and 31 shows the eleventh form of embodiment of the present invention as an example in which the power supply housing 2a and the chemical receptacle retainer 2b that make up the cartridge 2 are made separate and can be disjoinably joined together. The chemical receptacle retainer 2b is formed at its end with a pair of engagement projections 22 for engagement with corresponding holes 33 formed in the apparatus main body 1. It also has a pair of rails 23a and 23a formed on its lower opposite sides for engagement with corresponding grooves 34 and 34 formed in the apparatus main body 1 in its lower inside opposite surfaces.

On the other hand, the power supply housing 2a on has a pair of rails 23b and 23b formed on its outer opposite sides for engagement with the grooves 34 and 34 in the apparatus main body 1, with which the rails 23a and 23a on the chemical receptacle retainer 2b are designed to also engage.

In the construction mentioned above, the cartridge 2 is assembled with the apparatus main body 1 first by bringing the chemical receptacle retainer 2b loaded with the chemical receptacle 3 into engagement with the apparatus main body, this by engaging the engagement projections 22 with the corresponding holes 33 and engaging the two rails 23a and 23a with the corresponding grooves 34 and 34.

Then, the power supply housing 2a is inserted into the apparatus main body 1 first by engaging the two rails 23b and 23b with the corresponding grooves 34 and 34 and sliding those rails in these grooves until the end of the power supply housing 2a comes in contact with the lower surface of the chemical receptacle retainer 2b. Then, the hook 20 formed on the outer wall 17 of the battery case 13 in the power supply housing 2a is brought into engagement with the engagement protrusion piece 19 in the apparatus main body 1 to complete assembling the power supply housing 2a into the apparatus main body 1.

This form of embodiment enables the power supply housing 2a and the chemical receptacle retainer 2b to be exchanged individually with respect to the apparatus main body 1.

Further, while in the various forms of embodiment of the present invention described in the foregoing the chemical receptacle is shown to be engaged with and thereby held by the apparatus main body by means of the chemical receptacle retainer, it is also possible to make the chemical receptacle and the chemical receptacle retainer in one piece or integrated. It is further possible to make the chemical receptacle loadable directly into the apparatus main body without intermediary of the chemical receptacle retainer.

For the chemical, i.e., the active ingredient, employed in each of the various forms of embodiment of the invention described above, use may be made of an aromatic or fragrant agent, a deodorant, a microbicide, an acaricide, a harmful insect or animal repellent, an insecticide, an insectifuges, an insect growth control agent, a sucking action inhibitor or the like, which is volatile, singly or in a combination.

For example, in killing insects, any one or more of a variety of volatile insecticides so far used may be utilized. Illustrative are pyrethroid insecticides, carbamate insecticides and organophosphorus insecticides Pyrethroid insecticides are known to be high in safety and have been used well, of which preferred examples are listed below, each given in the order of the general name, the chemical and the parenthesized trade name followed by the producer.

allethrin: d1-3-allyl-2-methyl-4-oxo-2-cyclopentenyl d1-cis/trans-chrysanthemat (Pynamin, Sumitomo Chemical Co.)

d1•d-T80-allethrin: d1-3-allyl-2-methyl-4-oxo-2-cyclopentenyl d-cis/trans-chrysanthemat (Pynamin forte, Sumitomo Chemical Co.)

d1•d-T-allethrin: d1-3-allyl-2-methyl-4-oxo-2-cyclopentenyl d-trans chrysanthemat (Bioallethrin)

d•d-T-allethrin: d-3-allyl-2-methyl-4-oxo-2-cyclopentenyl d-trans chrysanthemat (Esbiol)

d•d-T80-prallethrin: (+)-2-methyl-4-oxo-3-(2-propionyl)-2-cyclopentenyl (+)-cis/trans-chrysanthemat (Etoc, Sumitomo Chemical Co.)

resmethrin: 5-benzyl-3-furylmethyl d1-cis/trans-chrysanthemat (Chrythron, Sumitomo Chemical Co.)

d•d-T80-resmethrin: 5-benzyl-3-furylmethyl d-cis/trans-chrysanthemat (Chrythron forte, Sumitomo Chemical Co.)

empenthrin: 1-ethynyl-2-methyl-2-pentenyl d1-cis/trans-3-(2,2-dimethyl vinyl)-2,2-dimethyl-1-cyclopropane carboxylate (Vaporthrin, Sumitomo Chemical Co.)

terallethrin: d1-3-allyl-2-methyl-4-oxo-2-cyclopentenyl-d1-cis/trans-2,2,3,3-tetramethyl-cyclopropane carboxylate (Knoxthrin, Sumitomo Chemical Co.)

phthalthrin: N-(3,4,5,6-tetrahydrophthalimide)-methyl d1-cis/trans chrysanthemat (Neopynamin, Sumitomo Chemical Co.)

d•d-T80-phthalthrin: (1,3,4,5,6,7 -hexahydro-1,3-dioxo-2-indolyl)methyl d1-cis/trans-chrysanthemat (Neopynamin forte, Sumitomo Chemical Co.)

furamethrin: 5-propargyl-2-furylmethyl d-cis/trans-chrysanthemat (Pynamin D, Sumitomo Chemical Co.)

permethrin: 3-phenoxybenzyl dl-cis/trans-3-(2,2-dichlorovinyl)-2,2-dimethyl-1-cyclopropanecarboxylate (Eksmin, Sumitomo Chemical Co.)

phenothrin: 3-phenoxybenzyl d-cis/trans-chrysanthemat (Sumithrin, Sumitomo Chemical Co.)

imiprothrin: 2,4-dioxo-1-(prop-2-inyl)-imidazolidine-3-yl methyl (1R)-cis/trans-chrysanthemat (Pralle, Sumitomo Chemical Co.)

fenvalerate: α-cyano-3-phenoxybenzyl-2-(4-chlorophenyl)-3-methyl butylate (Sumicidin, Sumitomo Chemical Co.)

cypermethrin: α-cyano-3-phenoxybenzyl d1-cis/trans-3-(2,2-dichlorovinyl)-2,2-dimethyl cyclopropane carboxylate (Agrothrin, Sumitomo Chemical Co.)

cyphenothrin: (±) α-cyano-3-phenoxybenzyl (+)-cis/trans-chrysanthemat (Gokilaht, Sumitomo Chemical Co.)

ethofenprox: 2-(4-ethoxyphenyl)-2-methyl propyl-3-phenoxybenzyl ether (Trebon)

tefluthrin: 2,3,5,6-tetrafluoro-4-methyl benzyl-3-(2-chloro-3,3,3-trifluoro-1-propenyl)-2,2-dimethyl-1-cyclopropane carboxylate fenpropathrin: α-cyano-3-phenoxybenzyl cis/trans-2,2,3,3-tetramethyl cyclopropane carboxylate fenfluthrin: 2,3,4,5,6-pentafluorobenzyl-d1-cis/trans-3-(2,2-dichlorovinyl)-2,2'-dimethyl-1-cyclopropane carboxylate 1-ethynyl-2-methyl-2-pentenyl cis/trans-2,2,3,3-tetramethyl-1-cyclopropane carboxylate For specific examples of the organophosphorus insecticides may be listed the following:

diazinon: (2-isopropyl-4-methyl pyrimidil-6)-diethyl thiophosphate (Diazinon)

fenitrothion, MEP; O,O-dimethyl-O-(3-methyl-4-nitrophenyl)thiophosphate (Sumithion)

pyridaphention; O,O-dimethyl-O-(3-oxo-2-phenyl-2H-pyridazin-6-yl)phosphorothioate (Ofunack)

malathion: dimethyl dicarbetoxy ethyl dithiophosphate (Malathon)

dipterex: O,O-dimethyl-2,2,2-trichloro-1-hydroxyethyl phosphonate chlorpyrifos: O,O-dimethyl-O-(3,5,6-trichlor-2-pyridyl)-phosphorothioate fenthion: O,O-dimethyl-O-(3-methyl-4-methylthiophenyl)-phosphorothioate (Baytex)

dichlorvos: O,O-dimethyl-2,2-dichlorovinylphosphate (DDVP)

propetamphos: O-[(E)-2-isopropoxycarbonyl-1-methylvinyl]-O-methylethylphosphoramidethioate (Safurotin)

Abate: O,O,O',O'-tetramethyl-O,O'-thiodi-P-phenylene phosphorothioate prothiofos: dithiophosphoric acid O-2,4-dichlorophenyl O-ethyl S-propyl ester (Tokuthion)

phoxim: O,O-diethyl-O-(α-cyano benzylidene amino) thiophosphate

For oxadiazol insecticides may be listed the following:

methoxadiazone: 5-methoxy-3-(2-methoxyphenyl)-O-1,3,4-oxadiazol-2-(3H)-one (Elemic)

For chloro nicotine insecticides may be listed the following:
  imidacloprid: 1-(6-chloro-3-pyridylmethyl)-N-nitro imidazolidin -2-ylideneamine (Admire)
  acetamiprid: (E)-N$^1$-[(6-chloro-3-pyridyl)methyl]-N$^2$-cyano-N$^1$-methyl acetone amidine (Mospilan)
For specific examples of the growth control agent may be listed the following:
  pyriproxyfen: 4-phenoxy phenyl (RS)-2-(2-pyridyl oxy) propyl ether
  methoprene: 11-methoxy-3,7,11-trimethyl-2,4-dodecadienoic acid-1-methyl ethyl ester
  hydroprene: ethyl(2E, 4E)-3,7,11-trimethyl-2,4-dodecadienoate
  phenoxy carb: ethyl[2-(4-phenoxy phenoxy)ethyl]carbamate
For specific examples of the insect repellent may be listed the following:
  N,N-diethyl-m-toluamid (deet)
  dimethyl phthalate
  dibuthyl phthalate
  2-ethyl-1,3-hexane diol
  1,4,4a, 5a, 6,9,9a, 9b-octahydrodibenzofuran-4a-carbardehyde
  di-n-propyl isothinchomeronate
  p-dichloro benzene
  di-n-butyl succinate
  diethyl amid caprate
  N-propyl acetanilide
  β-naphthol
  camphor In addition to an anti-oxidizing agent and an ultraviolet absorbing agent for preventing degradation of the active ingredient described, there may be incorporated an inhibitor, depressor and/or retardant for adjusting the amount of volatilization of the active ingredient, a substance or substances having a function or functions of giving out fragrance, deodorizing and/or sterilizing as desired in accordance with the present invention. Also, an aromatic or fragrant agent, adeodorant, a microbicide each can be singly volatilized in the nature of things.

Although the present invention has been described hereinbefore in terms of the presently preferred forms of embodiments with respect to or embodied in a fan type chemical diffusing apparatus, a chemical receptacle therefor and a clip type fastening device therefor, it is to be understood that such disclosure is purely illustrative and is not to be interpreted as limiting. Consequently, without departing from the spirit and scope of the invention, various alterations, modifications, and/or alternative applications of the invention will, no doubt, be suggested to those skilled in the art after having read the preceding disclosure. Accordingly, it is intended that the following claims be interpreted as compassing all alterations, modifications, or alternative applications as fall within the true spirit and scope of the invention.

What is claimed is:

1. A fan type chemical diffusing apparatus, comprising:
  a chemical receptacle for accommodating a chemical impregnated body therein that is impregnated with a volatile chemical, the chemical receptacle having vent holes;
  a chemical receptacle retainer for holding said chemical receptacle;
  a power supply housing for receiving a power supply therein; and
  an apparatus main body including: a fan for producing an airflow, a motor which is powered by said power supply for driving the fan, a switch for turning on and off current conduction to said motor, an inner airflow opening and an outer airflow opening disposed in a front face and a side face of said apparatus main body, respectively, for permitting the airflow produced by said fan to pass therethrough, an L-shaped recessed portion continuously formed in said apparatus main body from a front side through a lower side thereof, which is adapted to be loaded with said chemical receptacle retainer and said power supply housing, and an electrical connector which, when said power supply housing that is loaded into a lower portion of said recessed portion of said apparatus main body, is brought into contact with said power supply received in said power supply housing to establish electrical connection between said power supply and said switch;
  wherein said chemical receptacle retainer and said power supply housing are adapted to be detachably loaded in a front portion and the lower portion of said recessed portion of said apparatus main body, respectively, and when loaded in the recessed portion the chemical receptacle retainer and the power supply housing are positioned so as to receive essentially no limitation in volume from each other.

2. A fan type chemical diffusing apparatus as set forth in claim 1, wherein said chemical receptacle retainer and said power supply housing are integral with each other and form a cartridge, which is adapted to be disengageably inserted into and engaged with, so as to be loaded in, said recessed portion of said apparatus main body.

3. A fan type chemical diffusing apparatus as set forth in claim 1, wherein said chemical receptacle retainer and said power supply housinq are adapted to be disengageably inserted into and engaged with, so as to be loaded in, said recessed portion of said apparatus main body separately from each other.

4. A fan type chemical diffusing apparatus as set forth in claim 1, wherein said chemical receptacle is integral with said chemical receptacle retainer.

5. A fan type chemical diffusing apparatus as set forth in claim 1, wherein said apparatus main body includes an unloading mechanism for releasing engagement of at least one of said power supply housing and said chemical receptacle retainer loaded in said apparatus main body.

6. A fan type chemical diffusing apparatus as set forth in claim 1, wherein said power supply housing includes a power supply accommodating section that is positioned so as not to be contacted by the airflow passing through said chemical receptacle.

7. A fan type chemical diffusing apparatus as set forth in claim 1, further comprising a timer incorporated in said apparatus main body for establishing a time period of operation of said motor.

8. A fan type chemical diffusing apparatus as set forth in claim 1, wherein said power supply comprises a battery.

9. A fan type chemical diffusing apparatus as set forth in claim 8, wherein said battery, when accommodated in said power supply housing, is partially exposed to outside of said power supply housing.

10. A fan type chemical diffusing apparatus as set forth in claim 8, wherein said power supply housing is adapted to accommodate therein a battery case for said battery, such that said battery case is insertable as a drawer into said power supply housing.

11. A fan type chemical diffusing apparatus as set forth in claim 8, wherein said power supply housing is adapted to accommodate therein a battery case for the battery, and a cut-out is formed in the battery case to permit the electrical connector disposed in said apparatus main body to contact a battery terminal of the battery in said battery case.

12. A fan type chemical diffusing apparatus as set forth in claim 8, wherein said battery has an exhaustion point that is coincident with an end point of depletion of said chemical impregnated in the chemical impregnated body of the chemical receptacle.

13. A fan type chemical diffusing apparatus as set forth in claim 1, wherein at least one of said power supply housing and said chemical receptacle retainer is adapted to be loaded into said apparatus main body by sliding into the apparatus main body via a slide system to be engaged with the apparatus main body.

14. A fan type chemical diffusing apparatus as set forth in claim 13, wherein said slide system includes:
   a pair of slide engagement members provided at opposite sides of said at least one of said power supply housing and said chemical receptacle retainer along a direction in which said at least one of said power supply housing and said chemical receptacle retainer is slid into said apparatus main body; and
   a pair of counterparts to the slide engagement members provided at opposite sides of said apparatus main body along said direction.

15. A fan type chemical diffusing apparatus as set forth in claim 1, wherein said chemical receptacle is adapted to be detachably loaded into said chemical receptacle retainer from an outside of said chemical receptacle retainer.

16. A fan type chemical diffusing apparatus as set forth in claim 1, further comprising at least one of: (i) a hood which covers said outer airflow opening in said apparatus main body, and (ii) a hood which covers an outer airflow opening formed in said chemical receptacle retainer and an exposed region of said chemical receptacle when said chemical receptacle is held by said chemical receptacle retainer.

17. A fan type chemical diffusing apparatus as set forth in claim 1, wherein said fan is adapted to send the airflow towards said chemical receptacle, and a heater is disposed between said chemical receptacle and said fan.

18. A fan type chemical diffusing apparatus as set forth in claim 1, wherein said chemical receptacle comprises a first chemical receptacle which includes one end face that lies outside of said chemical receptacle retainer when said first chemical receptacle is held by said chemical receptacle retainer, and a second chemical receptacle; and
   wherein the apparatus further comprises a coupling member to couple the second chemical receptacle to said one end face of said first chemical receptacle.

19. A fan type chemical diffusing apparatus as set forth in claim 1, wherein said chemical receptacle has a variable volume.

20. A fan type chemical diffusing apparatus as set forth in claim 1, wherein said chemical receptacle comprises a shutter, which is fitted on one end face thereof, for controlling a rate of flow of air passing through said chemical receptacle.

21. A fan type chemical diffusing apparatus as set forth in claim 1, wherein said chemical receptacle comprises:
   a cylindrical receptacle main body including a cylindrical wall closed at a first end by an end wall in which a plurality of vent holes are formed; and
   a cylindrical lid body including a cylindrical wall closed at one end by an end wall in which a plurality of vent holes are formed,
   wherein the cylindrical wall of said lid body is adapted to be fitted into the cylindrical wall of said receptacle main body so as to be fitted with an inner surface of the cylindrical wall of said receptacle main body, and said end wall of said lid body includes a flange which contacts a surface of a second end of the cylindrical wall of said receptacle main body.

22. A fan type chemical diffusing apparatus as set forth in claim 21, wherein axially opposite end portions of the chemical receptacle are identical in shape.

23. A fan type chemical diffusing apparatus as set forth in claim 1, further comprising a member attached to a rear surface of said apparatus main body to at least one of suspend said apparatus main body from, and fix said apparatus main body fast to, another body or object.

24. A fan type chemical diffusing apparatus as set forth in claim 23, wherein said member comprises a clip fastening device comprising a clip member in the form of a tongue attached to an outer wall of the apparatus main body,
   wherein the clip member comprises a plurality of pressure foot portions which are adapted to be so hung on an object such that at least a portion of the object is inserted and gripped between the outer wall of the apparatus main body and the pressure foot portions so as to fasten the fan type chemical diffusing apparatus to the object,
   wherein the pressure foot portions are spaced apart from each other in a direction perpendicular to a direction of insertion of the object, and
   wherein at least one raised portion is provided on said outer wall as to be positioned between adjacent pressure foot portions.

25. A fan type chemical diffusing apparatus as set forth in claim 24, wherein said clip member further comprises a root and an end portion which are positioned at substantially a same distance from said outer wall.

26. A fan type chemical diffusing apparatus as set forth in claim 24, wherein at least one of an inner surface area of said pressure foot portions of said clip member, a surface area of said outer wall that opposes the inner surface area of said pressure foot portions, and a surface area of said raised portion, is made uneven to provide a slip resistance for the object.

* * * * *